US009018179B2

(12) United States Patent
Kay et al.

(10) Patent No.: US 9,018,179 B2
(45) Date of Patent: Apr. 28, 2015

(54) METHODS AND COMPOSITIONS FOR RNAI MEDIATED INHIBITION OF GENE EXPRESSION IN MAMMALS

(75) Inventors: Mark Kay, Los Altos, CA (US); Anton McCaffrey, Pacifica, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 253 days.

(21) Appl. No.: 12/368,082

(22) Filed: Feb. 9, 2009

(65) Prior Publication Data

US 2009/0264505 A1 Oct. 22, 2009

Related U.S. Application Data

(63) Continuation of application No. 10/259,226, filed on Sep. 27, 2002, which is a continuation-in-part of application No. 10/200,002, filed on Jul. 19, 2002, now abandoned.

(60) Provisional application No. 60/360,664, filed on Feb. 27, 2002.

(51) Int. Cl.
| | |
|---|---|
| *C12N 15/11* | (2006.01) |
| *C12N 15/113* | (2010.01) |
| *A01K 67/027* | (2006.01) |
| *A61K 31/70* | (2006.01) |
| *A61K 38/00* | (2006.01) |
| *A61K 48/00* | (2006.01) |

(52) U.S. Cl.
CPC ........ *C12N 15/1131* (2013.01); *A01K 67/0275* (2013.01); *A01K 2217/075* (2013.01); *A61K 31/70* (2013.01); *A61K 38/00* (2013.01); *A61K 48/00* (2013.01); *C12N 2310/111* (2013.01); *C12N 2310/14* (2013.01); *C12N 2310/53* (2013.01)

(58) Field of Classification Search
USPC ....................................................... 514/44 A
See application file for complete search history.

(56) References Cited

U.S. PATENT DOCUMENTS

| | | |
|---|---|---|
| 5,610,050 A | 3/1997 | Blum et al. |
| 5,728,822 A | 3/1998 | Macfarlane |
| 5,922,687 A | 7/1999 | Mann et al. |
| 5,981,279 A | 11/1999 | Weiss |
| 5,985,847 A | 11/1999 | Carson et al. |
| 6,001,990 A | 12/1999 | Wands et al. |
| 6,030,954 A | 2/2000 | Wu et al. |
| 6,080,727 A | 6/2000 | Zupi |
| 6,107,027 A | 8/2000 | Kay et al. |
| 6,114,167 A | 9/2000 | Symonds et al. |
| 6,174,868 B1 | 1/2001 | Anderson et al. |
| 6,506,559 B1 * | 1/2003 | Fire et al. ............................ 435/6 |
| 6,573,099 B2 | 6/2003 | Graham |
| 8,067,383 B2 * | 11/2011 | Graham et al. ............. 514/44 R |
| 2002/0086356 A1 | 7/2002 | Tuschl et al. |
| 2002/0132788 A1 | 9/2002 | Lewis et al. |
| 2003/0018923 A1 | 1/2003 | Kumar et al. |
| 2003/0108923 A1 | 6/2003 | Tuschl et al. |
| 2003/0124513 A1 | 7/2003 | McSwiggen |
| 2003/0139363 A1 | 7/2003 | Kay et al. |
| 2003/0153519 A1 | 8/2003 | Kay et al. |
| 2003/0206887 A1 | 11/2003 | Morrissey et al. |
| 2004/0001811 A1 | 1/2004 | Kreutzer et al. |
| 2004/0221337 A1 | 11/2004 | Baulcombe et al. |
| 2004/0259247 A1 | 12/2004 | Tuschl et al. |

FOREIGN PATENT DOCUMENTS

| | | |
|---|---|---|
| CA | 2 359 180 A1 | 8/2000 |
| CA | 2 432 341 A1 | 7/2002 |
| CA | 2 432 350 A1 | 7/2002 |
| DE | 199 56 568 A1 | 8/2000 |
| DE | 101 00 586 C1 | 4/2002 |
| DE | 101 00 588 A1 | 7/2002 |
| DE | 200 231 25 U1 | 5/2003 |
| ES | 2 040 615 A1 | 10/1993 |
| JP | H09-216825 A | 8/1997 |
| JP | 2005-517427 | 6/2005 |
| WO | WO 90/11092 A1 | 10/1990 |
| WO | WO 92/16661 A1 | 10/1992 |
| WO | 98/44953 A1 | 10/1998 |
| WO | WO 99/32619 A1 | 7/1999 |

(Continued)

OTHER PUBLICATIONS

McCaffrey et al. (Nature Biotech. (2003), vol. 21, pp. 639-644).*
Liu et al. (Gene Therapy (1999), vol. 6, pp. 1258-1266).*
McCaffrey et al. (Nature (2002) vol. 418, pp. 38-39).*
Paddison et al. (Genes Dev. (2002), vol. 16, pp. 948-958).*
Hiroyuki Nakai, et al., "Unrestricted Heaptocyte Transduction with Adeno-Associated Virus Serotype 8 Vectors in Mice," Journal of Virology, (Jan. 2005), 79(1): 214-224.
Acsadi et al., "Direct gene transfer and expression into rat heart in vivo", *The New Biologist*, 3(1):71-81 (1991).
Adams, Amy, "RNA Therapeutics Enter Clinical Trials", *The Scientist*, 19(1):4 pages (2005).
Agami, R., "RNAi and related mechanisms and their potential use for therapy", *Current Opinion in Chemical Biology*, 6:829-834 (2002).
Agrawal et al., "Antisense therapeutics: is it as simple as complementary base recognition?", *Molecular Medicine Today*, 6:72-81 (2000).
Arias, C.F. et al., "RNA Silencing of Rotavirus Gene Expression", *Virus Research*, 102(1):43-51 (Abstract only) (2004).

(Continued)

*Primary Examiner* — Jon E Angell
(74) *Attorney, Agent, or Firm* — Kyle A. Gurley; Bret E. Field; Bozicevic, Field & Francis LLP

(57) ABSTRACT

Methods and compositions are provided for modulating, e.g., reducing, expression of a target sequence in mammals and mammalian cells. In the subject methods, an effective amount of an RNAi agent, e.g., an interfering ribonucleic acid (such as an siRNA or shRNA) or a transcription template thereof, e.g., a DNA encoding an shRNA, is introduced into a target cell, e.g., by being administered to a mammal that includes the target cell, e.g., via a hydrodynamic administration protocol. Also provided are RNAi agent pharmaceutical preparations for use in the subject methods. The subject methods and compositions find use in a variety of different applications, including academic and therapeutic applications.

15 Claims, 12 Drawing Sheets

(56) References Cited

FOREIGN PATENT DOCUMENTS

| WO | WO 99/49029 A1 | 9/1999 |
| --- | --- | --- |
| WO | 99/58694 A1 | 11/1999 |
| WO | WO 00/63364 A2 | 10/2000 |
| WO | WO 01/32223 A1 | 5/2001 |
| WO | WO 01/36646 A1 | 5/2001 |
| WO | WO 01/68836 A2 | 9/2001 |
| WO | WO 01/70949 A1 | 9/2001 |
| WO | 01/75164 | 10/2001 |
| WO | WO 02/44321 A2 | 6/2002 |
| WO | WO 02/055693 A2 | 7/2002 |
| WO | WO 03/006477 A1 | 1/2003 |

OTHER PUBLICATIONS

Barik, S., "Control of Nonsegmented Negative-Strand RNA Virus Replication by siRNA", *Virus Research*, 102(1):27-35 (Abstract only) (2004).

Bass et al., "Double-Stranded RNA as a Template for Gene Silencing", 101:235-238 (2000).

Bass, B.L., "RNA interference. The short answer", *Nature*, 411:428-429 (2001).

Bernstein et al., "The rest is silence", *RNA*, 7:1509-1521 (2001).

Bernstein et al., "Role for a bidentate ribonuclease in the initiation step of RNA interference", *Letters to Nature*, 49:363-366 (2001).

Billy et al., "Specific interference with gene expression induced by long, double-stranded RNA in mouse embryonal teratocarcinoma cell lines", *Proc. Natl. Acad. Sci. U.S.A.*, 98(25):14428-14433 (2001).

Bitko et al., "Phenotypic silencing of cytoplasmic genes using sequence specific double-stranded short interfering RNA and its application in the reverse genetics of wild type negative-strand RNA viruses", *BMC Microbiology* 2001, 1, http://www.biomedoentratcom/147-2180/1/34 (2001).

Boden, D. et al., "Enhanced Gene Silencing of HIV-1 Specific siRNA Using MicroRNA Designed Hairpins", *Nucleic Acids Research*, 32(3):1154-1158 (2004).

Cameron, C.E. and Castro, C., "The mechanism of action of ribavirin: lethal mutagenesis of RNA virus genomes mediated by the viral RNA-dependent RNA polymerase", *Current Opinion in Infectious Diseases*, 14(6):757-764 (2001).

Caplen et al., "Specific inhibition of gene expression by small double-stranded RNAs in invertebrate and vertebrate systems", *Proc. Natl. Acad. Sci. U.S.A.*, 98(17):9742-9747 (2001).

Caplen, N.J. et al., "RNAi as a gene therapy approach", *Expert Opinion on Biological Therapy*, 3:575-586 (2002).

Caplen, N.J. et al., "dsRNA-mediated gene silencing in cultured *Drosophila* cells: a tissue culture model for the analysis of RNA interference", *Gene*, 252(1-2):95-105 (2000).

Chang et al., "Replication of the human hepatitis delta virus genome is initiated in mouse hepatocytes following intravenous injection of naked DNA or RNA sequences", *Journal of Virology*, 75(7):3469-3473 (2001).

Chang, J. et al., "Susceptibility of Human Hepatitis Delta Virus RNAs to Small Interfering RNA Action", *Journal of Virology*, 77(1):9728-9731 (2003).

Check, E. "Gene regulation: RNA to the rescue", *Nature*, 425(6953):10-12 (2003).

Clemens et al., "Use of Double-Stranded RNA Interference in *Drosophila* Cell Lines to Dissect Signal Transduction Pathways", *Proc. Natl. Acad. Sci. U.S.A.*, 97(12):6499-6503 (2000).

Coburn, G.A. et al., "siRNAs: a new wave of RNA-based therapeutics", *Journal of Antimicrobial Chemotherapy*, 51:753-756 (2003).

European Search Report for EP application No. 02 761 123.5, Search Report dated Aug. 18, 2008, 4 pages (2008).

International Search report for PCT application PCT/US03/30574, search report dated Mar. 17, 2005, 5 pages (2005).

Elbashir et al., "Functional anatomy of siRNAs for mediating efficient RNAi in *Drosophila melanogastar* embryo lysate", *The EMBO Journal*, 20(23):6877-6888 (2001).

Elbashir et al., "Duplexes of 21-nucleotide RNAs mediate RNA interference in cultured mammalian cells", *Nature*, 411:494-498 (2001).

Furukawa et al., "BTB protein Keap1 targets antioxidant transcription factor Nrf2 for ubiquitination by the Cullin 3-Roc1 ligase", *Molecular and Cellular Biology*, 25(1):162-171 (2005).

Gitlin et al., "Short interfering RNA confers intracellular antiviral immunity in human cells", *Nature*, 418:430-434 (2002).

Gondi et al., "RNAi-mediated inhibition of cathepsin B and uPAR leads to decreased cell invasion, angiogenesis and tumor growth in gliomas", *Oncogene*, 23:8486-8496 (2004).

Grimm et al., "Adeno-Associated Virus Vectors for Short Hairpin RNA Expression", *Methods in Enzymology*, 392:381-405 (2005).

Hammond et al., "An RNA-directed nuclease mediates past-transcriptional gene silencing in *Drosophila* cells", *Letters to Nature*, 404:293-296 (2000).

Hammond et al., "Argonaute2, a link between Genetic and Biochemical Analyses of RNA", *Science*, 293:1146-1150 (2001).

Hammond et al., "Post-transcriptional gene silencing by double-stranded RNA", *Nature reviews*, 2:110-119 (2001).

Hickman et al., "Gene expression following direct injection of DNA into liver", *Human Gene Therapy*, 5. 1477-1453 (1994).

Hilla Giladi, et al, "Small Interfering RNA Inhibits Hepatitis B Virus Replication in Mice", *Molecular Therapy*, 8(5);769-776 (Abstract only) (2003).

Jan Kronke, et al., "Alternative Approached for Efficient Inhibition of Hepatitis C Virus RNA Replication by Small Interfering RNAs", *Journal of Virology*, (78)7:3436-3446 (2004).

Kanda, T. et al., "Interference of Hepatitis A Virus Replication by Small Interfering RNAs", *Biochemical and Biophysical Research Communications*, 318(2):341-345 (Abstract only) (2004).

Kennerdel et al., "Heritable Gene Silencing in *Drosophila* Using Double Stranded RNA", *Nature Biotechnology*, 17:896-898 (2000).

Kobayashi et al., "Vector-based in vivo RNA interference: dose- and time-dependent suppression of transgene expression", *Nucleic Acids Research*, 308(2):688-693 (2004).

Lakka, S.S. et al., "Inhibition of cathepsin B and MMP-9 gene expression in glioblastoma cell line via RNA interference reduces tumor cell invasion, tumor growth and angiogenesis", *Oncogene*, 23:4681-4689 (2004).

Li et al., "Lentiviral vector delivery of recombinant small interfering RNA expression cassettes", *Methods in Enzymology*, 392:381-405 (2005).

Liu et al., "Hydrodynamics-based transfection in animals by systemic administration of plasmid DNA", *Gene Therapy*, 6:1258-1266 (1999).

Liu, F. et al., "Hydrodynamics-based transfection in animals by systemic administration of plasmid DNA", *Gene Therapy*, 6(7):1258-1266 (1999).

McCaffrey et al., "Determinants of hepatitis C translational initiation in vitro, in cultured cells and mice", *Molecular Therapy*, 5(6): 676-684 (2002).

McCaffrey et al., "RNA interference in adult mice", *Nature*, 418:38-39 (2002).

McCown, M. et al., "The Utility of siRNA Transcripts Produced by RNA Potyrnerase I in Down Regulating Viral Gene Expression and Replication of Negative-and positive-strand RNA Viruses", *Virology*, 313(2):514-524 (Abstract only) (2003).

Opalinska, J.B. and Gewirtz, A.M., "Nucleic-acid therapeutics: basic principles and recent applications", *Nature Review*, 1:504-514 (2002).

Paddison et al., "Short hairpin RNAs (shRNAs) induce sequence-specific silencing in mammalian cells", *Genes & Development*, 16:948-98 (2002).

Paddison et al., "Stable suppression of gene expression by RNAi in mammalian cells", *Proc. Natl. Acad. Sci. U.S.A.*, 99(3):1443-1448 (2002).

Paul, C.P. et al., "Effective expression of small interfering RNA in human cells", *Nature Biotechnology*, 20(5):505-508 (2002).

Paul, C.P. et al., "Effective Expression of Small Interfering RNA in Human cells", *Nature Biotechnology*, 29:505-508 (2002).

(56) References Cited

OTHER PUBLICATIONS

Pusch, O. et al., "Nucleotide Sequence Homology Requirement of HIV-1-Specific Short Hairpin RNA", *Nucleic Acids Research*, 31(22):6444-6449 (2003).
R. Carthew, "Gene silencing by double-stranded RNA", *Current Opinion in Cell Biology*, 13:244-248 (2001).
Randall, G. et al., "Clearance of Replicating Hepatitis C Virus Replicon RNAs in Cell Culture by Small Interfering RNAs", *Proc Natl. Acad. Sci. U.S.A.*, 100(1):235-240 (2003).
Randall, G. et al., "Interfering with Hepatitis C Virus RNA Replication", *Virus Research*, 102:19-25 (2004).
Robbins et al., "Sensing the Danger in RNA", *Nature Medicine*, 11(3):250-251 (2005).
Sambrook et al., Molecular Cloning: A Laboratory Manual $2^{nd}$ Ed. Cold Springs Harbor Laboratory Press, pp. 7.3-7.5 (1989).
Scherer, L. et al., "RNAi Applications in Mammalian Cells", *Bio Techniques*, 36(4):557-561 (2004).
Smalheiser et al., "RNAi and Brain Function: was McConnell on the right Track?", *Trends Neurosciences*, 24(4):216-218 (2001).
Song et al., "RNA Interference Targeting FAS Products Mice From Fulminant Hepatitis", *Nature Medicine*, 9(3):347-351 (1999).
Sui et al., "A DNA vector-based RNAi technology to suppress gene expression in mammalian cells", *Proc. Natl. Acad. Sci. U.S.A.*, 99(8):5515-5520 (2002).
Svoboda et al. "Selective reduction of dormant maternal mRNAs in mouse oocytes by RNA interference" *Development*, 127:4147-4156 (2000).
Svoboda et al., "RNAi in mouse oocytes and preimplantatlon embryos: effectiveness of hairpin dsRNA", *Biochemical and Biophysical Research Communications*, 287:1099-1104 (2001).
Takigawa, Y. et al., "Suppression of Hepatitis C Virus Replicon by RNA Interference Directed Against the NS3 and NS5B Regions of the Viral Genorne", *Microbiol. Immunol.*, 48(8):591-598 (2004).
Tompkins, S.M., "Protection Against Lethal Influenza Virus Challenge by RNA Interference in Vivo", *Proc. Natl. Acad. Sci. U.S.A.*, 101(23):8682-8686.
Venkatesan et al., "Structure and Function of a small RNA that selectively inhibits internal ribosome entry site-mediated translation", *Nucleic Acids Research*, 27(2):562-572 (1999).
Wang et al., "RNA Interference Targeting FAS Products Mice From Fulminant Hepatitis", *Breast Cancer Research*, 7(2):220-228 (2004).
Wang Z. et al., "Inhibition of Severe Acute Respiratory Syndrome Virus Replication by Small Interfering RNAs in Mammalian Cells", *Journal of Virology*, 78(14):7523-7527 (2004).
Wianny et al., "Specific interference with gene function by double-stranded RNA in early mouse development", *Nature Cell Biology*, 2:70-75 (2000).
Wolff et al., "Direct gene transfer into mouse muscle in vivo", *Science*, 247:1465-1468 (1990).

Yang et al., "Short RNA duplexes produced by hydrolysis with *Escherichia coli* RNase III mediate effective RNA interference in mammalian cells", *Proc. Natl. Acad. Sci. U.S.A.*, 99(15):9942-9947 (2000).
Ying, C. et al., "Selective Inhibition of Hepatitis B Virus Replication by RNA Interference", *Biochemical and Biophysical Research Communications*, 309:(2)482-484 (Abstract only) (2003).
Yokota, T. et al., "Inhibition of Intracellular Hepatitis C Virus Replication by Synthetic and Vector-Derived Small Interfering RNAs", *EMBO Reports*, 4(6):602-608 (2003).
Zhang et al., "In Vivo Knockdown of Gene Expression in Brain Cancer With Intravenous RNAi in Adult rats", *The Journal of Gene Medicine*, 5:1039-1045 (2003).
Zhang et al., "Targeted Gene Silencing by Small Interfering RNA based Knock Down Technology", *Current. Pharmaceutical Biotechnology*, 5:1-7 (2004).
Zhang et al., "High levels of foreign gene expression in hepatocytes after tail vein injections of naked plasmid DNA", *Human Gene Therapy*, 10:1735-1737 (1999).
Zhang et al., "Long-term expression of human alpha t-antitrypsin gene in mouse liver achieved by intravenous administration of plasmid DNA using a hydrodynamics-based procedure", *Gene Therapy*, 7:1344-1349 (2000).
Zhang, J. et al., "Down-Regulation of Viral Replication by Adenoviral-Medicated Expression of siRNA Against Cellular Cofactors for Hepatitis C Virus", *Journal of Virology*, 320:135-143 (2004).
Japanese Office Action for Japanese Patent Application No. 2003-515539, Office Action dated Feb. 12, 2009, 9 pages (2009).
Elbashir, S.M. et al., "RNA Interference is Mediated by 21- and 22-nucleotide RNAs", *Genes & Development*, 15:188-200 (2001).
Tuschl et al., "The siRNA user guide", 5 pages, revised Aug. 26, 2001, accessed on Nov. 11, 2001 from http://www.mpibpc.gwdg.de/abtielungen/100/105/sirna_u.html.
Abdelgany et al., "Allele-specific silencing of a pathogenic mutant acetylcholine receptor subunit by RNA interference", Human Molecular Genetics, vol. 12, No. 20, pp. 2637-2644 (2003).
Calegari et al., "Tissue-specific RNA interference in postimplantation mouse embryos with endoribonuclease-prepared short interfering RNA", PNAS, vol. 99, No. 22, pp. 14236-14240 (2002).
Hamasaki et al., "Short interfering RNA-directed inhibition of hepatitis B virus replication", FEBS Letters vol. 543, pp. 51-54 (2003).
Manche et al., "Interactions between double-stranded RNA regulators and the protein kinase DAI", Molecular and Cellular Biology, vol. 12, No. 11, pp. 5238-5248 (1992).
Zender et al., "Caspase 8 small interfering RNA prevents acute liver failure in mice", PNAS, vol. 100, No. 13, pp. 7797-7802 (2003).
McCaffrey; et al. "In vivo delivery of siRNA" Exprimental Medicine, Japan (2004), 22(4):485-491.
Smith; et al. "Total silencing by intron-spliced hairpin RNAs" Nature (Sep. 2000), 407(6802):319-320.

* cited by examiner

SP6 control RNA
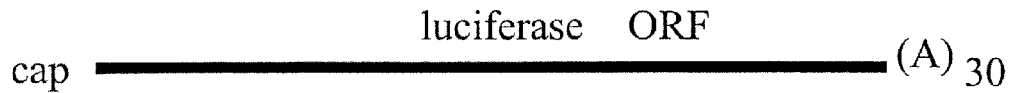
ACCATG RNA
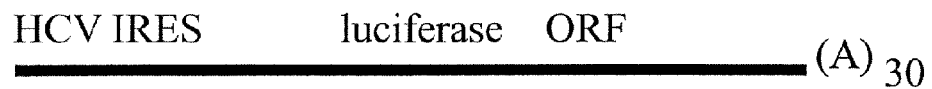
pHCV Dual Luc DNA
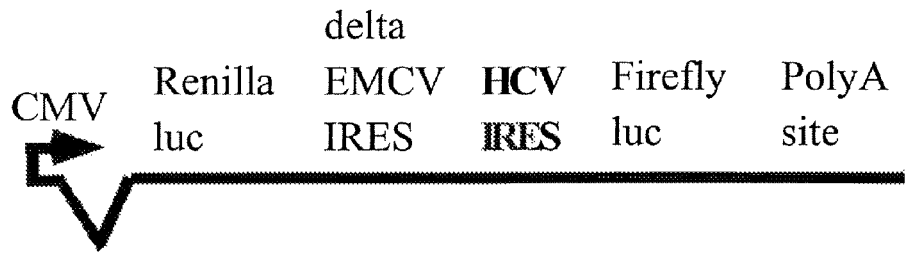
pEMCV Dual Luc DNA
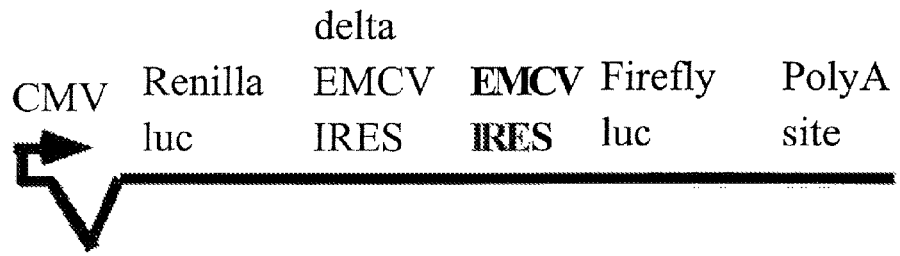
pCMVGL3 DNA
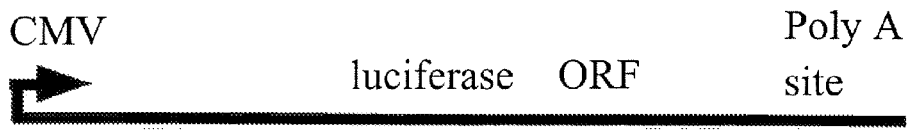
Figure 3

Antisense + Target 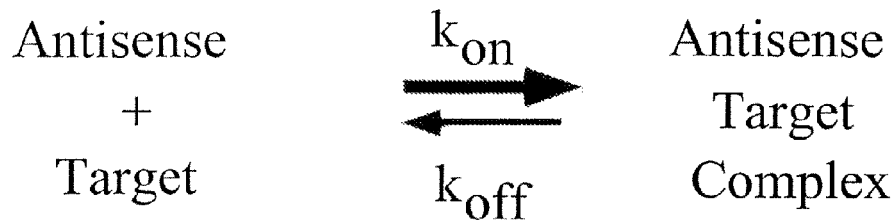 Antisense Target Complex
$$K = \frac{k_{on}}{k_{off}}$$  $k_{on}$ is diffusion controlled largely length independent
Long Oligo  Non-specific  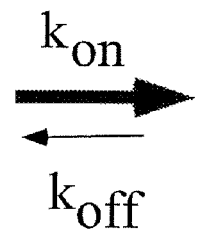
Short Oligo  Ineffective  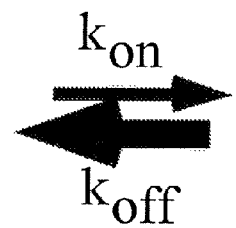
Optimal Oligo  Just Right  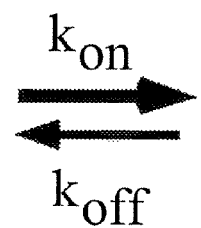
Figure 4

SEQUENCE LISTING

```
<160> NUMBER OF SEQ ID NOS: 21

<210> SEQ ID NO 1
<211> LENGTH: 21
<212> TYPE: RNA
<213> ORGANISM: Artificial Sequence
<220> FEATURE:
<223> OTHER INFORMATION: oligonucleotide

<400> SEQUENCE: 1
ucgaaguacu cagcguaagu u                                                   21

<210> SEQ ID NO 2
<211> LENGTH: 21
<212> TYPE: RNA
<213> ORGANISM: Artificial Sequence
<220> FEATURE:
<223> OTHER INFORMATION: oligonucleotide

<400> SEQUENCE: 2
cuuacgcuga guacuucgau u                                                   21

<210> SEQ ID NO 3
<211> LENGTH: 21
<212> TYPE: RNA
<213> ORGANISM: Artificial Sequence
<220> FEATURE:
<223> OTHER INFORMATION: oligonucleotide

<400> SEQUENCE: 3
cuuacgcuga guacuucgau u                                                   21

<210> SEQ ID NO 4
<211> LENGTH: 21
<212> TYPE: RNA
```

```
<213> ORGANISM: Artificial Sequence
<220> FEATURE:
<223> OTHER INFORMATION: oligonucleotide

<400> SEQUENCE: 4
uugaaugcga cucaugaagc u                                              21

<210> SEQ ID NO 5
<211> LENGTH: 21
<212> TYPE: RNA
<213> ORGANISM: Artificial Sequence
<220> FEATURE:
<223> OTHER INFORMATION: oligonucleotide

<400> SEQUENCE: 5
agcuucauaa ggcgcaugcu u                                              21

<210> SEQ ID NO 6
<211> LENGTH: 21
<212> TYPE: RNA
<213> ORGANISM: Artificial Sequence
<220> FEATURE:
<223> OTHER INFORMATION: oligonucleotide

<400> SEQUENCE: 6
uuucgaagua uuccgcguac g                                              21

<210> SEQ ID NO 7
<211> LENGTH: 23
<212> TYPE: RNA
<213> ORGANISM: Artificial Sequence
<220> FEATURE:
<223> OTHER INFORMATION: oligonucleotide

<400> SEQUENCE: 7
cugugagauc uacggagccu guu                                            23

<210> SEQ ID NO 8
<211> LENGTH: 23
<212> TYPE: RNA
<213> ORGANISM: Artificial Sequence
<220> FEATURE:
<223> OTHER INFORMATION: oligonucleotide

<400> SEQUENCE: 8
uugacacucu agaugccucg gac                                            23

<210> SEQ ID NO 9
<211> LENGTH: 33
<212> TYPE: RNA
<213> ORGANISM: Artificial Sequence
<220> FEATURE:
<223> OTHER INFORMATION: oligonucleotide

<400> SEQUENCE: 9
ggauuccaau ucagcgggag ccaccugaug aag                                 33

<210> SEQ ID NO 10
<211> LENGTH: 36
<212> TYPE: RNA
<213> ORGANISM: Artificial Sequence
<220> FEATURE:
<223> OTHER INFORMATION: oligonucleotide

<400> SEQUENCE: 10
uaaccuaagg uugagucgcu cucgguggge uaguuc                              36
```

```
<210> SEQ ID NO 11
<211> LENGTH: 66
<212> TYPE: RNA
<213> ORGANISM: Artificial Sequence
<220> FEATURE:
<223> OTHER INFORMATION: oligonucleotide

<400> SEQUENCE: 11
ggucgaagua ucagcguaa gugaugucca cuuaaguggg uguuguuugu guugggguguu    60 uugguu                                                              66

<210> SEQ ID NO 12
<211> LENGTH: 78
<212> TYPE: RNA
<213> ORGANISM: Artificial Sequence
<220> FEATURE:
<223> OTHER INFORMATION: oligonucleotide

<400> SEQUENCE: 12
gggauggacg auggccuuga ucuuguuuac cgucacaccc accacuggga gauacaagau    60
caaggccauc gucuuccu                                                 78

<210> SEQ ID NO 13
<211> LENGTH: 35
<212> TYPE: DNA
<213> ORGANISM: Artificial Sequence
<220> FEATURE:
<223> OTHER INFORMATION: oligonucleotide

<400> SEQUENCE: 13
gaggtttagg aggctagcta caacgatcgt gctca                              35

<210> SEQ ID NO 14
<211> LENGTH: 25
<212> TYPE: DNA
<213> ORGANISM: Artificial Sequence
<220> FEATURE:
<223> OTHER INFORMATION: oligonucleotide

<400> SEQUENCE: 14
tctttgaggt ttaggattcg tgctc                                         25

<210> SEQ ID NO 15
<211> LENGTH: 25
<212> TYPE: DNA
<213> ORGANISM: Artificial Sequence
<220> FEATURE:
<223> OTHER INFORMATION: oligonucleotide

<400> SEQUENCE: 15
tcgtggtgga cttctctcaa ttttc                                         25

<210> SEQ ID NO 16
<211> LENGTH: 25
<212> TYPE: DNA
<213> ORGANISM: Artificial Sequence
<220> FEATURE:
<223> OTHER INFORMATION: oligonucleotide

<400> SEQUENCE: 16
ctcagtttac tagtgccatt tgttc                                         25

<210> SEQ ID NO 17
```

```
<211> LENGTH: 25
<212> TYPE: DNA
<213> ORGANISM: Artificial Sequence
<220> FEATURE:
<223> OTHER INFORMATION: oligonucleotide

<400> SEQUENCE: 17
atgatgtggt attgggggcc aagtc                                           25

<210> SEQ ID NO 18
<211> LENGTH: 25
<212> TYPE: DNA
<213> ORGANISM: Artificial Sequence
<220> FEATURE:
<223> OTHER INFORMATION: oligonucleotide

<400> SEQUENCE: 18
tggccaaaat tcgcagtccc caacc                                           25

<210> SEQ ID NO 19
<211> LENGTH: 25
<212> TYPE: DNA
<213> ORGANISM: Artificial Sequence
<220> FEATURE:
<223> OTHER INFORMATION: oligonucleotide

<400> SEQUENCE: 19
tccccgtctg tgccttctca tctgc                                           25

<210> SEQ ID NO 20
<211> LENGTH: 25
<212> TYPE: DNA
<213> ORGANISM: Artificial Sequence
<220> FEATURE:
<223> OTHER INFORMATION: oligonucleotide

<400> SEQUENCE: 20
cctagaagaa gaactccctc gcctc                                           25

<210> SEQ ID NO 21
<211> LENGTH: 25
<212> TYPE: DNA
<213> ORGANISM: Artificial Sequence
<220> FEATURE:
<223> OTHER INFORMATION: oligonucleotide

<400> SEQUENCE: 21
agaagatctc aatctcggga atctc                                           25
```

METHODS AND COMPOSITIONS FOR RNAI MEDIATED INHIBITION OF GENE EXPRESSION IN MAMMALS

CROSS-REFERENCE TO RELATED APPLICATIONS

This application is a continuation application of application Ser. No. 10/259,226 filed on Sep. 27, 2002, which is a continuation-in-part application of application Ser. No. 10/200,002 filed on Jul. 19, 2002; which application (pursuant to 35 U.S.C. § 119 (e)) claims priority to the filing date of the U.S. Provisional Patent Application Ser. No. 60/307,411 filed Jul. 23, 2001 and U.S. Provisional Patent Application Ser. No. 60/360,664 filed Feb. 27, 2002; the disclosures of each of which are herein incorporated by reference.

REFERENCE TO SEQUENCE LISTING, TABLE OR COMPUTER PROGRAM

A "Sequence Listing" has been submitted with this application in the form of a text file, created 22 Jun. 2009, and named "586008254 US04 seqlist.txt" (8170 bytes), the contents of which are incorporated herein by reference in their entirety.

FEDERALLY-SPONSORED RESEARCH OR DEVELOPMENT

This invention was made with Government support under contract AI004132awarded by the National Institutes of Health. The Government has certain rights in this invention.

INTRODUCTION

1. Field of the Invention
The field of this invention is RNAi.
2. Background of the Invention
Double-stranded RNA induces potent and specific gene silencing through a process referred to as RNA interference (RNAi) or posttranscriptional gene silencing (PTGS). RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger.

RNAi has become the method of choice for loss-of-function investigations in numerous systems including, *C. elegans, Drosophila*, fungi, plants, and even mammalian cell lines. To specifically silence a gene in most mammalian cell lines, small interfering RNAs (siRNA) are used because large dsRNAs (>30 bp) trigger the interferon response and cause nonspecific gene silencing.

Increasingly, RNAi is being looked to as a potential therapeutic agent for use in treating' a variety of different disease conditions. As such, of interest in the continued identification of disease conditions that may be treated by RNAi.

RELEVANT LITERATURE

WO 01/68836. See also: Bernstein et al., RNA (2001) 7: 1509-1521; Bernstein et al., Nature (2001) 409:363-366; Billy et al., Proc. Nat'l Acad. Sci USA (2001) 98:14428-33; Caplan et al., Proc. Nat'l Acad. Sci USA (2001) 98:9742-7; Carthew et al., Curr. Opin. Cell Biol (2001) 13: 244-8; Elbashir et al., Nature (2001) 411: 494-498; Hammond et al., Science (2001) 293:1146-50; Hammond et al., Nat. Ref. Genet. (2001) 2:110-119; Hammond et al., Nature (2000) 404:293-296; McCaffrey et al., Nature (2002): 418-38-39; and McCaffrey et al., Mol. Ther. (2002) 5:676-684; Paddison et al., Genes Dev. (2002) 16:948-958; Paddison et al., Proc. Nat'l Acad. Sci USA (2002) 99:1443-48; Sui et al., Proc. Nat'l Acad. Sci USA (2002) 99:5515-20.

U.S. patents of interest include U.S. Pat. Nos. 5,985,847 and 5,922,687. Also of interest is WO/11092. Additional references of interest include: Acsadi et al., New Biol. (January 1991) 3:71-81; Chang et al., J. Virol. (2001) 75:3469-3473; Hickman et al., Hum. Gen. Ther. (1994) 5:1477-1483; Liu et al., Gene Ther. (1999) 6:1258-1266; Wolff et al., Science (1990) 247: 1465-1468; and Zhang et al., Hum. Gene Ther. (1999) 10:1735-1737: and Zhang et al., Gene Ther. (1999) 7:1344-1349.

SUMMARY OF THE INVENTION

Methods and compositions are provided for modulating, e.g., reducing, viral gene expression in mammals and mammalian cells. In the subject methods, an effective amount of an RNAi agent, e.g., an interfering ribonucleic acid (such as an siRNA or shRNA) or a transcription template thereof, e.g., a DNA encoding an shRNA, is administered to a mammal, e.g., via a hydrodynamic administration protocol. Also provided are RNAi agent pharmaceutical preparations for use in the subject methods. The subject methods and compositions find use in a variety of different applications, including research and therapeutic applications, such as the treatment of a host by inhibition of viral replication.

BRIEF DESCRIPTION OF THE FIGURES

FIG. 2A) Representative images of light emitted from mice co-transfected with the luciferase plasmid pGL3-Control and either no siRNA (left), luciferase siRNA (middle) or unrelated-siRNA (right). A pseudocolor image representing intensity of emitted light (red most and blue least intense) superimposed on a grayscale reference image (for orientation) shows that RNAi functions in adult mammals. Forty µg of annealed 21-mer siRNAs (Dharmacon) were co-injected into the livers of mice with the 2 µg of pGL3-Control DNA and 800 units of RNasin (Promega) in 1.8 ml of PBS in 5-7 seconds. Seventy two hours after the original injection, mice were anesthetized and given 3 mg of luciferin intraperitoneally 15 min prior to imaging. FIG. 2B) Summary of siRNA data. Mice receiving luciferase siRNA emitted significantly less light than untreated controls. A one-way ANOVA analysis, with a post hoc Fisher's test was conducted. The untreated and unrelated-siRNA groups were statistically similar. FIG. 2C) pShh1-Ff1 (center) but not pShh1-Ff1 rev (right) reduced luciferase expression in mice compared to the untreated control (left). 10 µg of pShh1-Ff1 or pShh1-rev were co-injected with 40 µg of pLuc-NS5B in 1.8 ml of PBS. FIG. 2D) Quantitation of pShh1 data. Animals were treated according to NIH Guidelines for Animal Care and the Guidelines of Stanford University.

FIG. 3 provides a schematic representation of the constructs employed in the morpholino phosphoramidate antisense HCV inhibition assay performed in the Experimental Section, below.

FIG. 4 provides background information of the mechanism of antisense inhibitors.

DEFINITIONS

Figure 1:
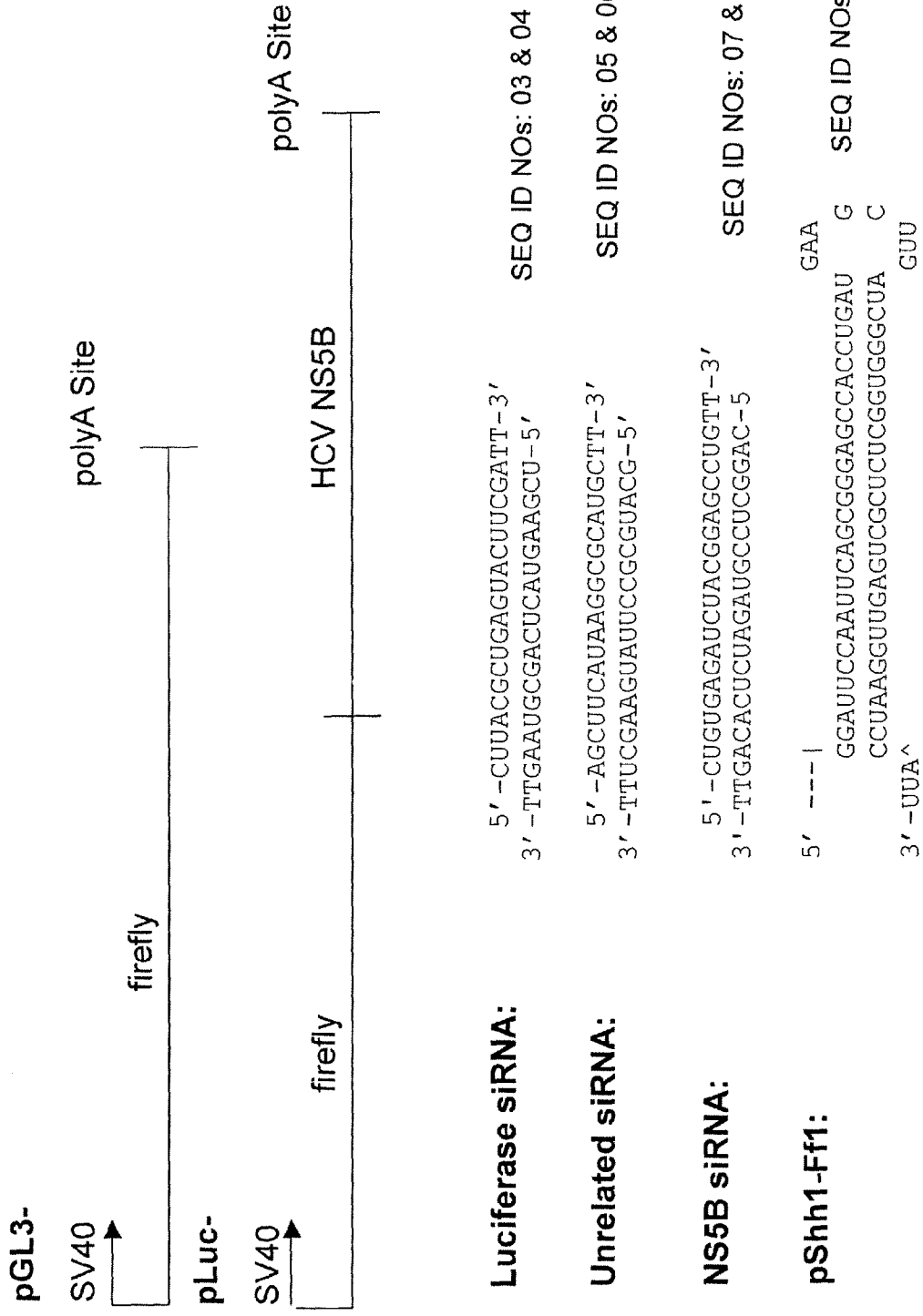
FIG. 1 provides expression constructs employed in the RNAi experiments described below.

For convenience, certain terms employed in the specification, examples, and appended claims are collected here.

As used herein, the term "vector" refers to a nucleic acid molecule capable of transporting another nucleic acid to which it has been linked. One type of vector is a genomic integrated vector, or "integrated vector", which can become integrated into the chromsomal DNA of the host cell. Another type of vector is an episomal vector, i.e., a nucleic acid capable of extra-chromosomal replication in an appropriate host, e.g., a eukaryotic or prokaryotic host cell. Vectors capable of directing the expression of genes to which they are operatively linked are referred to herein as "expression vectors". In the present specification, "plasmid" and "vector" are used interchangeably unless otherwise dear from the context.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, that may optionally include intron sequences that are derived from chromosomal DNA. The term "intron" refers to a DNA sequence present in a given gene that is not translated into protein and is generally found between exons. As used herein, the term "transfection" means the introduction of a nucleic acid, e.g., an expression vector, into a recipient cell by nucleic acid-mediated gene transfer.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

Likewise, "encodes", unless evident from its context, will be meant to include DNA sequences that encode a polypeptide, as the term is typically used, as well as DNA sequences that are transcribed into inhibitory antisense molecules.

The term "loss-of-function", as it refers to genes inhibited by the subject RNAi method, refers a diminishment in the level of expression of a gene when compared to the level in the absence of the RNAi agent.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

By "recombinant virus" is meant a virus that has been genetically altered, e.g., by the addition or insertion of a heterologous nucleic acid construct into the particle.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a dsRNA construct.

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct when the nucleic acid construct is capable of being inherited by daughter cells.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct that is heterologously expressed in a cell.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

As used herein, "proliferating" and "proliferation" refer to cells undergoing mitosis.

As used herein, "immortalized cells" refers to cells that have been altered via chemical, genetic, and/or recombinant means such that the cells have the ability to grow through an indefinite number of divisions in culture.

The "growth state" of a cell refers to the rate of proliferation of the cell and the state of differentiation of the cell.

"Inhibition of gene expression" refers to the absence (or observable decrease) in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radiolmmunoassay (RIA), other immunoassays, and fluorescence activated cell analysis (FACS). For RNA-mediated inhibition in -a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of administered active agent and longer times after administration of active agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

DESCRIPTION OF THE SPECIFIC EMBODIMENTS

Methods and compositions are provided for modulating, e.g., reducing, viral gene expression in mammalian cells, e.g., as found in a mammalian host. In the subject methods, an effective amount of an RNAi agent, e.g., an interfering ribonucleic acid (such as an siRNA or shRNA) or a transcription template thereof, e.g., a DNA encoding an shRNA, is contacted with the target mammalian cells, e.g., via administeration to a mammalian host that includes the target cells, e.g., via a hydrodynamic administration protocol. Also provided are RNAi agent pharmaceutical preparations for use in the subject methods. The subject methods and compositions find use in a variety of, different applications, including academic and therapeutic applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices and materials are now described.

All publications mentioned herein are incorporated herein by reference for the purpose of describing and disclosing the components that are described in the publications which might be used in connection with the presently described invention.

RNAi Inhibition of Viral Gene Expression

As summarized above, the subject invention provides methods of performing RNAi mediated inhibition of viral gene expression in mammals and mammalian cells, including non-embryonic mammals. In further describing this aspect of the subject invention, the subject methods are described first in greater detail, followed by a review of various representative applications in which the subject invention finds use as well as kits that find use in practicing the subject invention.

Methods

As indicated above, one aspect of the subject invention provides methods of employing RNAi to modulate expression of a viral target gene or genes in a mammalian cell or mammalian host including such a cell harboring such a target viral genome. In many embodiments, the subject invention provides methods of reducing viral gene expression of one or more target genes in a mammalian host organism. By reducing expression is meant that the level of expression of a target gene or coding sequence is reduced or inhibited by at least about 2-fold, usually by at least about 5-fold, e.g., 10-fold, 15-fold, 20-fold, 50-fold, 100-fold or more, as compared to a control. By modulating expression of a target gene is meant altering, e.g., reducing, transcription/translation of a coding sequence, e.g., genomic DNA, mRNA etc., into a polypeptide, e.g., protein, product. In many embodiments, the subject invention provides methods of reducing or inhibiting viral replication of one or more target genes in a mammalian host organism. By reducing replication is meant that the level of replication of a target viral genome is reduced or inhibited by at least about 2-fold, usually by at least about 5-fold, e.g., 10-fold, 15-fold, 20-fold, 50-fold, 100-fold or more, as compared to a control. In certain embodiments, the replication of the target viral genome is reduced to such an extent that replication of the target viral genome is effectively inhibited.

The subject invention provides methods of reducing target viral gene expression in a mammalian cell or organism, where in certain embodiments the mammalian organism is a non-embryonic mammalian organism. By non-embryonic mammalian organism is meant a mammalian organism or host that is not an embryo, i.e., is at a stage of development that is later in time than the embryonic stage of development. As such, the host organism may be a fetus, but is generally a host organism in a post-natal stage of development, e.g., juvenile, adult, etc.

In practicing the subject methods, an effective amount of an RNAi agent is introduced into the target cell, e.g., via administration to the host organism including the target cell or cells, to modulate viral gene expression in a desirable manner, e.g., to achieve the desired reduction in target viral genome replication.

By RNAi agent is meant an agent that modulates expression of a target gene, e.g., a gene involved in viral replication, by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA (such as d-siRNA as described in copending application Ser. No. 60/377,704; the disclosure of which is herein incorporated by reference), the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

The RNAi agent can be administered to the non-embryonic mammalian host using any convenient protocol, where the protocol employed is typically a nucleic acid administration protocol, where a number of different such protocols are known in the art. The following discussion provides a review of representative nucleic acid administration protocols that may be employed. The nucleic acids may be introduced into tissues or host cells by any number of routes, including viral infection, microinjection, or fusion of vesicles. Jet injection may also be used for intra-muscular administration, as described by Furth et al. (1992), *Anal Biochem* 205:365-368. The nucleic acids may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. Expression vectors may be used to introduce the nucleic acids into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

For example, the RNAi agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

Depending on the nature of the RNAi agent, the active agent(s) may be administered to the host using any convenient means capable of resulting in the desired modulation of target gene expression. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Administration of an effective amount of an RNAi agent to a non-embryonic mammalian host according as described above results in a modulation of target gene(s) expression, e.g., a reduction of target gene(s) expression, as described above.

The above described methods work in any mammal, where representative mammals of interest include, but are not limited to: ungulates or hooved animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

The above-described methods find use in a variety of different applications, representative types of which are now described in greater detail below.

Utility

The subject methods find use in a variety of different applications, where representative applications include both academic/research applications and therapeutic applications. Each of these types of representative applications is described more fully below.

Academic/Research Applications

The subject methods find use in a variety of different types of academic, research applications, in which one desires to modulate expression of one or more target genes (coding sequences) in a mammalian host, e.g., to determine the function of a target gene/coding sequence in a mammalian host. The subject methods find particular use in "loss-of-function" type assays, where one employs the subject methods to reduce or decrease or inhibit expression of one or more target genes/coding sequences in a mammalian host.

As such, one representative utility of the present invention is as a method of identifying gene function in a non-embryonic mammal, where an RNAi agent is administered to a mammal according to the present invention in order to inhibit the activity of a target gene of previously unknown function. Instead of the time consuming and laborious isolation of mutants by traditional genetic screening, functional genomics using the subject methods determines the function of uncharacterized genes by administering an RNAi agent to reduce the amount and/or alter the timing of target gene activity. Such methods can be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with use of the subject methods to determine gene function in a live mammalian organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple representative assay inhibits gene expression according to the partial sequence available from an expressed sequence tag (EST). Functional alterations in growth, development, metabolism, disease resistance, or other biological processes would be indicative of the normal role of the EST's gene product. The function of the target gene can be assayed from the effects it has on the mammal when gene activity is inhibited.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be employed to produce an RNAi agent, which agent can then be administered to the mammal, and whether an alteration in the characteristic is correlated with inhibition can be determined.

The present invention is useful in allowing the inhibition of essential genes. Such genes may be required for organism viability at only particular stages of development or cellular compartments. The functional equivalent of conditional mutations may be produced by inhibiting activity of the target gene when or where it is not required for viability. The invention allows addition of an RNAi agent at specific times of development and locations in the organism without introducing permanent mutations into the target genome.

In situations where alternative splicing produces a family of transcripts that are distinguished by usage of characteristic exons, the present invention can target inhibition through the appropriate exons to specifically inhibit or to distinguish among the functions of family members. For example, a hormone that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone.

Therapeutic Applications

The subject methods also find use in a variety of therapeutic applications in which it is desired to modulate, e.g., one or more target viral genes, viral replication of a pathogenic virus, etc., in a whole mammal or portion thereof, e.g., tissue, organ, cell, etc. In such methods, an effective amount of an RNAi active agent is administered to the host mammal or introduced into the target cell. By effective amount is meant a dosage sufficient to modulate expression of the target viral gene(s), as desired, e.g., to achieve the desired inhibition of viral replication. As indicated above, in many embodiments of this type of application, the subject methods are employed to reduce/inhibit expression of one or more target viral genes in the host in order to achieve a desired therapeutic outcome.

Depending on the nature of the condition being treated, the target gene may be a gene derived from the cell, an endogenous gene, a pathologically mutated gene, e.g. a cancer causing gene, a transgene, or a gene of a pathogen which is present in the cell after infection thereof, e.g., a viral gene or genome, etc. Depending on the particular target gene and the dose of RNAi agent delivered, the procedure may provide partial or complete loss of function for the target gene. Lower doses of injected material and longer times after administration of RNAi agent may result in inhibition in a smaller fraction of cells.

The subject methods find use in the treatment of a variety of different conditions in which the modulation of target gene expression in a mammalian host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The present invention is not limited to modulation of expression of any specific type of target gene or nucleotide sequence. Representative classes of target genes of interest include but are not limited to: developmental genes (e.g., adhesion molecules, cyclin kinase inhibitors, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lyso/ymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5), the RNA component of telomerase, vascular endothelial growth factor (VEGF), VEGF receptor, tumor necrosis factors nuclear factor kappa B, transcription factors, cell adhesion molecules, Insulin-like growth factor, transforming growth factor beta family members, cell surface receptors, RNA binding proteins (e.g. small nucleolar RNAs, RNA transport factors), translation factors, telomerase reverse transcriptase); etc.

Where the target gene is a viral gene, e.g., where inhibition of viral replication is desired, the target viral gene/genome may be from a number of different viruses, where representative viruses include, but are not limited to: HBV, HCV, HIV, influenza A, Hepatitis A, poliovirus, enteroviruses, rhinoviruses, aphthoviruses, and the like Kits Also provided are reagents and kits thereof for practicing one or more of the above-described methods. The subject reagents and kits thereof may vary greatly. Typically, the kits at least include an RNAi agent as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Hydrodynamic Administration of Naked RNA

Also provided by the subject invention are methods and compositions for the in vivo introduction of a naked nucleic acid, e.g. ribonucleic acid, deoxyribonucleic or chemically modified nucleic acids (including, but not limited to, morpholino, peptide nucleic acids, methylphosphonate, phosphorothioate or 2'-Omethyl oligonucleotides), into the target cell of a vascularized organism, e.g. a mammal. These methods of the subject invention are conveniently referred to as "hydrodynamic" methods.

In one embodiment of the subject methods, an aqueous formulation of a naked nucleic acid and an RNase inhibitor is administered into the vascular system of the organism. In many embodiments, the aqueous formulation also includes a competitor ribonucleic acid, e.g. a non-capped non-polyadenylated ribonucleic acid. In yet other embodiments, codelivery of DNA capable of being transcribed into the RNA molecule with candidate modulatory agents is performed without an RNase inhibitor or competitor ribonucleic acid, where the modulatory agent and the DNA may or may not be delivered as a single composition. The subject methods find use in a variety of different applications, including both research and therapeutic applications, and are particularly suited for use in the in vivo delivery of a ribonucleic acid into a hepatic cell, e.g. for liver targeted in vivo delivery of nucleic acids.

In further describing this aspect of the subject invention, the subject methods will be described first followed by a description of representative applications in which the subject methods find use and kits for use in practicing the subject methods.

Methods

As summarized above, the subject invention provides a method for the in vivo introduction of a nucleic acid, e.g. a ribonucleic acid, into a target cell present in a vascularized multi-cellular organism. By in vivo introduction is meant that, in the subject methods, the target cell into which the nucleic acid is introduced is one that is present in the multi-cellular organism, i.e., it is not a cell that is separated from, e.g. removed from, the multi-cellular organism. As such, the subject methods are distinct from in vitro nucleic acid transfer protocols, in which a nucleic acid is introduced into a cell or cells separated from the multi-cellular organism from which they originated, e.g. are in culture. In other words, the subject methods are not methods of in vitro nucleic acid transfer.

By introduction of the nucleic acid is meant that the nucleic acid, e.g., deoxyribonucleic acid (DNA) or ribonucleic acid (RNA) or a non-naturally occurring nucleic acid analog, is inserted into the cytoplasm of the target cell. In other words, the nucleic acid is moved from the outside of the target cell to the inside of the target cell across the cell membrane.

By vascularized multi-cellular organism is meant a multi-cellular organism that includes a vascular system. Multi-cellular organisms of interest include plants and animals, where animals are of particular interest, particularly vertebrate animals that have a vascular system made up of a system of veins and arteries through which blood is flowed, e.g. in response to the beating of a heart. Animals of interest are mammals in many embodiments. Mammals of interest include; rodents, e.g. mice, rats; livestock, e.g. pigs, horses, cows, etc., pets, e.g. dogs, cats; and primates, e.g. humans. In certain embodiments, the multi-cellular organism is a human. In other embodiments, the multi-cellular organism is a non-human mammal, e.g. a rodent, such as a mouse, rat, etc.

As mentioned above, the subject methods are, in the broadest sense, suitable for introduction of nucleic acids into the target cell of a host. The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids. The terms "ribonucleic acid" and "RNA" as used herein mean a polymer composed of ribonucleotides. The terms "deoxyribonucleic acid" and "DNA" as used herein mean a polymer composed of deoxyribonucleotides.

The subject methods are particularly suited for use in the delivery of a ribonucleic acid into a target cell of a multi-cellular organism. As such, the methods will now be further described in terms of the delivery of ribonucleic acids. However, the following protocols are also suitable for use in the delivery of other nucleic acids, e.g. DNAs (such as plasmid DNA), etc.

In practicing the subject methods, an aqueous composition of the ribonucleic acid in which the ribonucleic acid is present as a naked ribonucleic acid is administered to the vascular system of the multi-cellular organism or host. In many embodiments, the naked RNA aqueous composition or formulation is administered to the vein of the host, i.e. the naked RNA formulation is intravenously administered. In certain embodiments, the naked RNA formulation is intravenously administered to the host via high pressure injection. By high pressure injection is meant that the aqueous formulation is intravenously introduced at an elevated pressure, where the elevated pressure is generally at least about 20, usually at least about 30 mmHg. In many embodiments, the elevated pressure ranges from about 10 to 50 mm Hg, where 40 to 50 mm Hg is often preferred. Methods of administering aqueous formulations under high pressure, such as those described above, are described in the references listed in the relevant literature section, supra., As mentioned above, the RNA or DNA that is to be introduced into the target cell via the subject methods is present in the aqueous formulation as naked RNA. By "naked" is meant that the RNA is free from any delivery vehicle that can act to facilitate entry into the target cell. For example, the naked RNAs or DNAs delivered in the subject methods are free from any material that promotes transfection, such as liposomal formulations, charged lipids or precipitating agents, e.g. they are not complexed to colloidal materials (including liposomal preparations). In addition, the naked RNAs of the subject invention are not contained in a vector that would cause integration of the RNA into the target cell genome, i.e. they are free of viral sequences or particles that carry genetic information.

The naked RNAs that may be delivered via the subject invention may vary widely in length, depending on their intended purpose, e.g. the protein they encode, etc. Generally, the naked RNAs will be at least about 10 nt long, usually at least about 30 nt long and more usually at least about 35 nt long, where the naked RNAs may be as long as 20,000 nt or longer, but generally will not exceed about 10,000 nt long and usually will not exceed about 6,000 nt long. In certain embodiments where the naked RNA is an RNAi agent, as described above, the length of the RNA ranges from about 10 to 50 nt, often from about 10 to 40 nt, and more often from about 15 to 30 nt, including 15 to 25 nt, such as 20 to 25 nt, e.g., 21 or 22 nt.

The naked RNAs that may be introduced into a target cell according to the subject methods may or may not encode a protein, i.e. may or may not be capable of being translated into a protein upon introduction into the target cell. In those embodiments where the naked RNA is capable of being translated into a protein following introduction into the target cell, the naked RNA may or may not be capped, it may include an IRES domain, etc. However, in many particular protocols of this embodiment, the naked RNA is capped. Furthermore, the RNA in these embodiments generally includes at least a polyadenylation signal, and in many embodiments is polyadenylated, where the polyA tail, when present, generally ranges in length from about 10 to 300, usually from about 30 to 50. Further description of the naked RNAs is provided infra.

As mentioned above, an aqueous formulation of the naked RNA is intravascularly, usually intravenously, administered to the host. In the aqueous formulations employed in the subject methods, an effective amount of the naked RNA is combined with an aqueous delivery vehicle. By effective amount is meant an amount that is sufficient to provide for the desired amount of transfer into the target cell, e.g. to provide the desired outcome, such as desired amount of protein expression. In many embodiments, the amount of naked RNA present in the aqueous formulation is at least about 5 micrograms, usually at least about 10 micrograms and more usually at least about 20 micrograms, where the amount may be as great as 10 milligrams or greater, but generally does not exceed about 1 milligram and usually does not exceed about 200 micrograms.

Aqueous delivery vehicles of interest include: water, saline and buffered media. Specific vehicles of interest include: sodium chloride solution, Ringer's dextrose, dextrose and sodium chloride, lactated Ringer's, phosphate buffered saline, etc. The aqueous delivery vehicles may further include preservatives and other additives, e.g. antimicrobials, antioxidants, chelating agents, inert gases, nutrient replenishers, electrolyte replenishers, divalent cations, such as magnesium, calcium and manganese, etc. Of particular interest in many embodiments is the use of buffered salt solutions are pseudo-physiological.

A feature of certain embodiments of the subject methods is that the naked RNA is introduced into the vascular system of the multi-cellular organism in combination with an RNase inhibitor. By RNase inhibitor is meant a compound or agent that at least reduces the activity of, if not completely inactivates, an RNase activity in the multi-cellular organism. In many embodiments, the RNase inhibitor is a protein inhibitor of RNase, where the human placental RNase inhibitor is of particular interest. The protein RNase inhibitor may be purified from a natural source or synthetically produced, e.g. via recombinant techniques. Human placental RNase inhibitor may be obtained from a variety of different sources under a variety of different tradenames, where representative sources include: Promega, Inc., Strategene, Inc., Fisher Scientific, Inc., and the like.

While the RNase inhibitor may, in certain embodiments, be administered to the host in a composition separate from the aqueous naked RNA composition, in many embodiments the RNase inhibitor is present in the aqueous naked RNA composition. The amount of RNase inhibitor that is present in the aqueous composition is sufficient to provide for the desired uptake of the naked RNA. Where the RNase inhibitor is a protein inhibitor, the concentration of the inhibitor in the aqueous composition that is introduced into the multi-cellular organism during practice of the subject methods may range from about 4 to 4,000 units, usually from about 400 to 4,000 units and more usually from about 400 to 1,500 units.

In certain embodiments, the naked RNA and RNase inhibitor are administered in conjunction with a competitor RNA. By competitor RNA is meant an RNA that is capable of serving as a competitive inhibitor of RNase activity. In many embodiments, the competitor RNA is uncapped and non-polyadenylated. By uncapped is meant that the competitor RNA lacks the cap structure found at the 5' end of eukaryotic messenger RNA, i.e. it lacks a 5' 7 methyl G. By non-polyadenylated is meant that the competitor RNA lacks a polyA tail or domain of polyadenylation at its 3' end, as is found in eukaryotic messenger RNA. The length of the competitor RNA may vary, but is generally at least about 70 nt, usually at least about 200 nt and more usually at least about 1,500 nt, where the length may be as great as 10,000 nt or greater, but generally does not exceed about 3,500 nt and usually does not exceed about 1,500 nt. The concentration of competitor RNA in the aqueous composition is sufficient to provide for the desired protection of the naked RNA (e.g. via competition for binding by RNase), and in many embodiments ranges from about 10 µg/ml to 10 mg/ml, usually from about 20 to 200 µg/ml and more usually from about 40 to 150 µg/ml.

The subject methods result in highly efficient transfer of the administered RNA into the cytoplasm of the target cell(s). The subject methods are particularly suited for transferring RNA into the cytoplasm of liver or hepatic cells and non-parenchymal cells in the liver. As such, in many embodiments the subject methods are in vivo methods 'of achieving high level nucleic acid, e.g. RNA, transfer into hepatic cells or liver tissue:

The nucleic acid that is introduced into the target cell via the subject methods is short lived once inside the target cell. Depending on the particular nature of the nucleic acid, the half life the nucleic acid following introduction via the subject methods generally ranges from about 30 sec to 10 days, usually from about 1 min to 24 hrs and more usually from about 5 min to 10 hrs. As such, where the nucleic acid is an RNA encoding a protein of interest, protein expression following introduction via the subject method is transient, typically lasting for a period of time ranging from about 1 min to 3 days, usually from about 5 min to 24 hrs. As such, in many embodiments of the subject methods, the subject methods are methods of providing for transient protein expression from a transgene, where protein expression is equal to RNA lifetime. Nonetheless, the protein expressed may have a longer lifetime, depending on the nature of the particular protein.

Utility

The subject methods find use in a variety of different applications in which the efficient in vivo transfer of a naked nucleic acid into a target cell is desired. Applications in which the subject methods find use include both therapeutic and research applications. Therapeutic applications of interest include gene therapy applications, vaccination applications, and the like. Research applications of interest include the production of animal models for particular conditions, e.g. RNA viral infections, the observation of gene expression on phenotypes to elucidate gene function, etc. Other applications in which the subject invention finds use include the development of antisense, ribozyme and chimeraplasty (i.e. the repair of genes via RNA/DNA chimeras (see e.g. Yoon et al., *Proc Natl Acad Sci USA* (1996) 93(5):2071-6; Cole-Strauss et al., *Science* (1996) 273(5280):1386-9; and Zhu et al., *Proc Natl Acad Sci USA* (1999) 96(15):8768-73) therapeutics, as well as interfering RNA (RNA whose presence in the cell prevents the translation of similar RNAs, (See e.g. Wianny et al., *Nat Cell Biol* (2000) 2(2):70-5; and SiQun et al., *Nature* (1998) 391: 806-811) therapeutics.

One type of application in which the subject methods find use is in the synthesis of polypeptides, e.g. proteins, of interest from a target cell, particularly the transient expression of a polypeptide. In such applications, a nucleic acid that encodes the polypeptide of interest in combination with requisite and/or desired expression components, e.g. 5' cap structures, IRES domains, polyA signals or tails, etc., is introduced into the target cell via in vivo administration to the multi-cellular organism in which the target cell resides, where the target cell is to serve as an expression host for expression of the polypeptide. For example, where the naked nucleic acid administered by the subject methods is RNA, the RNA is an RNA that is capable of being translated in the cytoplasm of the target cell into the protein encoded by the sequence contained in the RNA. The RNA may be capped or uncapped, where when it is uncapped it generally includes an IRES sequence. The RNA also generally further includes a polyA tail, where the length of the polyA tail typically ranges from about 10 to 300, usually from about 30 to 50 nt. Following in vivo administration and subsequent introduction into the target cell, the multi-cellular organism, and targeted host cell present therein, is then maintained under conditions sufficient for expression of the protein encoded by the transferred RNA. The expressed protein is then harvested, and purified where desired, using any convenient protocol.

As such, the subject methods provide a means for at least enhancing the amount of a protein of interest in a multi-cellular organism. The term 'at least enhance' includes situations where the methods are employed to increase the amount of a protein in a multi-cellular organism where a certain initial amount of protein is present prior to practice of the subject methods. The term 'at least enhance' also includes those situations in which the multi-cellular organism includes substantially none of the protein prior to practice of the subject methods. As the subject methods find use in at least enhancing the amount of a protein present in a multi-cellular organism, they find use in a variety of different applications, including pharmaceutical preparation applications and therapeutic applications, where the latter is described in greater detail infra.

Therapeutic applications in which the subject methods find use include gene therapy applications in which the subject methods are used to enhance the level of a therapeutic protein in the host organism and vaccination applications, in which the subject methods are used to vaccinate the host (or develop vaccines for delivery by other methods). As distinct from DNA based expression protocols, the subject RNA based expression protocols are uncomplicated by the need for promoter, enhancer, repressor and other regulatory elements commonly associated with eukaryotic genes. The subject methods may be used to deliver a wide variety of therapeutic nucleic acids which, upon entry into the target cell, provide for the requisite enhanced protein level in the host. Therapeutic nucleic acids of interest include nucleic acids that replace defective genes in the target host cell, such as those responsible for genetic defect based diseased conditions, by encoding products that are supposed to be provided to the host by these defective genes; nucleic acids which have therapeutic utility in the treatment of cancer; and the like. Representative products involved in gene defect disease conditions whose level may be enhanced by practicing the subject methods include, but are not limited to: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic nucleic acids that may be delivered via the subject methods include: nucleic acids that enhance the antitumor activity of lymphocytes by encoding appropriate factors, nucleic acids whose expression product enhances the immunogenicity of tumor cells, tumor suppressor encoding nucleic acids, toxin encoding nucleic acids, suicide factor encoding nucleic acids, multiple-drug resistance product encoding nucleic acids, ribozymes, DNA ribozymes, DNA/RNA chimeras, interfering RNA and anti-sense sequences, and the like.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to practice of the subject methods. In contrast, the naked nucleic acid compositions are administered directly to the multi-cellular organism and are taken up by the target cells, following which expression of the encoded product occurs.

As mentioned above, another therapeutic application in which the subject methods find use is in vaccination of a host (as well as development of a vaccine to be delivered by other methods). In these methods, the naked nucleic acid, e.g. RNA, that is administered to the host via the subject methods encodes a desired immunogen that, upon entry of the RNA into the target cell, is expressed and secreted to elicit the desired immune response. Vaccination methods in which naked nucleic acid are employed and in which the subject methods of naked nucleic acid delivery find use are further described in WO 90/11092, the disclosure of which is herein incorporated by reference.

As mentioned above, the subject methods also find use in various research applications. One research application in which the subject invention finds use is in the production of animal models of RNA virus infection, where RNA viruses of interest include: HCV, HIV, influenza A, Hepatitis A, poliovirus, enteroviruses, rhinoviruses, aphthoviruses, and the like. To produce such animal models, constructs are first provided that include one or more regulatory elements from the RNA virus of interest operably linked to a reporter domain, e.g., a domain encoding a detectable product (such as luciferase, a fluorescent protein, etc.); etc. Alternatively, DNA constructs that can be transcribed in vivo into such RNA constructs may be employed. These constructs are then administered to a host, e.g., a mouse, according to the subject methods to produce an animal model of an infection by the corresponding RNA virus. As such, also provided are the animal models of RNA viruses produced by the subject methods. A representative protocol for the production of an RNA virus animal model is provided in the experimental section infra.

Also provided are methods of screening candidate modulatory, e.g., enhancing or inhibitory, agents using such animal models. A variety of different types of candidate agents may be screened according to the subject methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Of particular interest in certain embodiments are antisense nucleic acids. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 16 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorodiamidate linkages, methylphosphonates phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3"-S-5"-O-phosphorothioate, 3'-CH$_2$-5'-O-phosphonate and 3'—NH-5'-O-phosphoroamidate. Peptide nucleic acids replace the entire ribose phosphodiester backbone with a peptide linkage. Sugar modifications are also used to enhance stability and affinity. One example is the substitution of the ribose sugar with a morpholine. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents of interest also include interfering ribonucleic acids, such as those described above.

In such screening assays, the nucleic acid construct (e.g., the RNA or DNA construct described above) and the candidate agent are administered to the host animal, the effect of the candidate agent on the activity of the construct is observed, and the observed effect is related to the modulatory activity of the candidate compound. The candidate agent and nucleic acid construct may be administered to the host according to the subject methods at the same or different times, where in certain preferred embodiments the two components are administered to the host simultaneously, e.g., in the form of a single fluid composition. Representative screening assays are provided in the experimental section infra.

Another research application in which the subject methods find use is the elucidation of gene function. In such methods, RNA having a particular gene sequence is introduced via the subject methods and the effect of the gene on the phenotype of the organism is observed. Benefits of using the subject methods for gene function research applications include the ability to express the genes without concern for genetic regulatory elements. Other research applications in which the subject methods find use include, but are not limited to: the study of ribozyme and antisense efficacy; the study of RNA metabolism, and the like.

The subject methods also find use in the delivery of RNAi therapeutic and/or research agents, including siRNA and shRNA, as described more fully above and in the experimental section, below.

Kits

Also provided by the subject invention are kits for use in practicing the subject methods of in vivo nucleic acid delivery to a target cell, e.g. hepatic cells. The subject kits generally include a naked nucleic acid that is desired to be introduced into the target cell and an RNase inhibitor. The subject kits may further include an aqueous delivery vehicle, e.g. a buffered saline solution, etc. In addition, the kits may include a competitor RNA, as described supra. In the subject kits, the above components may be combined into a single aqueous composition for delivery into the host or separate as different or disparate compositions, e.g. in separate containers. Optionally, the kit may further include a vascular delivery means for delivering the aqueous composition to the host, e.g. a syringe etc., where the delivery means may or may not be pre-loaded with the aqueous composition. In cases were the reporter gene is transcribed in vivo from a DNA, RNase inhibitor and competitor RNA are not required.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. RNAi in Mammals
A. We co-delivered a 2 micrograms of plasmid that expresses a luciferase mRNA (pCMVGL3) mixed with 1.8 ml PBS, 1200 units of RNasin and 40 micrograms of competitor RNA along with the following formulations:
   1) (Group 1 no RNA) 1.8 ml PBS as a untreated control;
   2) (Group 2 antisense RNA) 1.8 ml PBS mixed with 20 micrograms of antisense orientation 21 mer RNA/DNA chimera with the sequence 5'-UCGAAGUACU-CAGCGUAAGdTdT-3' (SEQ ID NO:01) (deoxythymidilate residues are indicated by dT, the remaining nucleotides are ribonucleotides); or
   3) (Group 3 RNAi) 1.8 ml PBS mixed with 20 micrograms of antisense 21 mer described above annealed to 20 micrograms of its sense complement (with sequence 5'-CU-UACGCUGAGUACUUCGAdTdT-3') (SEQ ID NO:02).

The oligonucleotides were kinased using adenosine triphosphate and T4 polynucleotide kinase. Each formulation (1-3) was tested by high pressure tail vein injection in 5 week old female Balb/c mice. At 5, 72 and 96 hours post injection, light emitted as a result of luciferase expression was measured as described above. The results of this experiment are summarized in the table below. Numbers expressed as relative light units.

|  | Group 1 no RNA | Group 1 standard error | Group 2 Antisense | Group 2 standard error | Group 3 RNAi | Group 3 standard error |
|---|---|---|---|---|---|---|
| 3 hours | $1.11 \times 10^9$ | $2.05 \times 10^8$ | $1.29 \times 10^9$ | $7.90 \times 10^7$ | $7.90 \times 10^8$ | $3.54 \times 10^7$ |
| 72 hours | $6.60 \times 10^6$ | $7.57 \times 10^5$ | $5.41 \times 10^6$ | $9.91 \times 10^5$ | $8.23 \times 10^5$ | $2.86 \times 10^5$ |
| 96 hours | $3.41 \times 10^6$ | $4.50 \times 10^5$ | $2.72 \times 10^6$ | $5.25 \times 10^5$ | $4.61 \times 10^5$ | $6.77 \times 10^4$ |

The above results demonstrate that RNAi (group 3) caused the destruction of luciferase RNA in the liver of an adult mammal. This destruction resulted in a decrease in light emitted as a result of luciferase activity when compared to animals that received no RNA or antisense oligonucleotide alone. To our knowledge, this is the first demonstration that RNAi is effective in an adult mammal. This method provides a model system to study the mechanism by which RNAi functions in a mammal. It is also useful for the development and optimization of RNAi based therapeutics. Furthermore, one need not codeliver the expression plasmid with the modulating agent. One could also deliver a modulating agent targeting an endogenous gene.

B. Here, we test the ability of RNAi to suppress gene expression in adult mammals. We find that synthetic small interfering RNAs (siRNAs) are potent inhibitors of gene expression in vivo. Furthermore, small-hairpin RNAs (shRNAs) are similarly effective. Notably, these RNAi agents can be delivered either as synthetic RNAs or transcribed in vivo from DNA expression constructs. These studies indicate that RNAi can be developed as a therapeutic tool and demonstrate that it can be employed with conventional gene-therapy strategies.

1. siRNAs
We modified existing hydrodynamic transfection methods J. Chang, L. J. Sigal, A. Lerro, J. Taylor, *J Virol* 75, 3469-73. (2001)) to permit efficient delivery of naked RNAs. Either an siRNA derived from firefly luciferase or an unrelated-siRNA were co-injected with a luciferase expression plasmid (construct description in FIG. 1). Luciferase expression was monitored in living animals using quantitative whole body imaging following injection of a luciferase substrate (4) and was dependent on the amount of reporter plasmid injected and the time after transfection (data not shown). Representative animals are shown in FIG. 2A. Quantification of these results is shown in FIG. 2B.

In each experiment, serum measurements of a co-injected plasmid encoding human α-1 antitrypsin (hAAT) (S. R. Yant, et al., *Nat Genet* 25, 35-41. (2000)) served as an internal control to normalize transfection efficiency and to monitor nonspecific translational inhibition. Average serum hAAT levels at 74 hours were similar in each group of animals.

Our results indicate specific siRNA-mediated inhibition of luciferase expression in adult mice ($p<0.0115$); unrelated-siRNAs were without effect ($p<0.864$). In 11 independent experiments, luciferase siRNAs reduced luciferase expression (emitted light) by an average of 81% (+/−2.2%).

2. shRNA
Short hairpin RNAs (shRNAs) targeting firefly luciferase of renilla luciferase were synthesized by T7 polymerase in vitro runoff transcription. Co-transfection of these in vitro transcribed RNAs with pGL3-Control DNA resulted in reduced firefly luciferase expression in culture (Paddison et al, Genes Dev. 16(8):948-58 (2002)). In order to test whether these hairpin RNAs were functional in mice, we hydrodynamically transfected 40 µg of in vitro transcribed luciferase shRNA (or as a control, renilla shRNA), 2 µg pGL3-Control DNA 2 µg pThAAT, 800 units of RNasin and 1.8 ml of PBS into mice. Light emitted from mice 72 hours after receiving firefly luciferase shRNAs was reduced by an average of 95% (+/−1.4%) compared to the untreated control. Light emitted from mice receiving the renilla shRNA was reduced only slightly. Surprisingly, co-transfection of T7 transcription template DNA with a plasmid expressing the T7 polymerase protein did not lead to any reduction in luciferase reporter activity in culture or in mice (data not shown).

Firefly Luciferase shRNA sequence (from 5' to 3')

(SEQ ID NO: 11)
GGUCGAAGUACUCAGCGUAAGUGAUGUCCACUUAAGUGGGUGUUGUUUGU

GUUGGGUGUUUUGGUU

*Renilla* Luciferase shRNA sequence (from 5' to 3')

(SEQ ID NO: 12)
GGGAUGGACGAUGGCCUUGAUCUUGUUUACCGUCACACCCACCACUGGGA

GAUACAAGAUCAAGGCCAUCGUCUUCCU

The above results demonstrate that short in vitro transcribed hairpins also reduced luciferase expression in vivo.

3. Conclusion

The above data demonstrate that RNAi can downregulate gene expression in adult mice.

C. Hepatitis C virus (HCV) is an RNA virus that infects 1 out of 40 people worldwide and is the most common underlying cause for liver transplantation in the western world. To determine whether RNAi could be directed against a human pathogen, several siRNAs were tested for their ability to target HCV RNAs in mouse liver. We used a reporter strategy in which HCV sequences were fused to luciferase RNA and RNAi was monitored by co-transfection in vivo. siRNAs targeting the HCV internal ribosome entry site and core protein coding region failed to inhibit luciferase expression. In contrast, siRNAs targeting the NS5B region of a chimeric HCV NS5B protein-luciferase fusion RNA reduced luciferase expression by 75% (+/−6.8%). These results indicate the utility of using RNAi therapeutically to target important human pathogens.

D. From these data, it is clear that siRNAs are functional in mice. Functional shRNAs, which are equally effective in inducing gene suppression, can be expressed in vivo from DNA templates using RNA polymerase III promoters (Paddison et al., submitted). Expression of a cognate shRNA (pShh1-Ff1) induced up to a 98% (+/−0.6%) suppression of luciferase expression, with an average suppression of 92.8% (+/−3.39%) in three independent experiments (FIGS. 2C and 2D). An empty shRNA-expression vector had no effect (data not shown). Furthermore, reversing the orientation of the shRNA (pShh1-Ff1 rev) insert abolished silencing, due to altered termination by RNA polymerase III and consequent production of an improperly structured shRNA (Paddison et al., submitted). These data indicate that plasmid-encoded shRNAs can induce a potent and specific RNAi response in adult mice. Furthermore, it demonstrates that this method of RNAi delivery can be tailored to take advantage of the significant progress that has been made in the development of gene-transfer vectors.

Existing gene therapy strategies depend largely upon the ectopic expression of exogenous proteins to achieve a therapeutic result. Since its discovery, RNAi has held the promise of complementing these gain-of-function approaches by providing a means for silencing disease-related genes. Considered together, our results indicate that RNAi can be induced in adult mammals using DNA constructs to direct the expression of small hairpin RNAs. These studies demonstrate that the present invention provides viral and non-viral delivery systems for application of therapeutic RNAi to a wide range of diseases.

II. Hydrodynamic Delivery of Naked RNA

A. Introduction

Unless otherwise noted, in all experiments RNAs and DNAs were added to the indicated amount of RNasin and brought to a final volume of PBS equal to 1.41.8 milliliters. This solution was injected into the tail vain of the mice in 4-5 seconds. All RNAs used in these studies were synthesized using an mMessage Machine kit and purified using an RNeasy kit (both from Qiagen Inc.). However, it should not be necessary to purify the RNA and other purification methods exist that should also work. RNasin used in all the experiments listed here was native RNasin purified from human placenta unless otherwise indicated (purchased from Promega Inc.). For luciferase samples, at the indicated time, mice were given an intraperitoneal injection of luciferin (1.5 micrograms/gram body weight) and the light emitted from the mouse was measured. Background is $-2 \times 10^2$ relative light units. Human factor IX samples were analyzed using an enzyme linked immunoassay.

B. Hydrodynamic Delivery of Naked RNA

RNAs coding for luciferase protein were injected into living mice with:

1) no RNase inhibitor; or
2) RNase inhibitor (called RNasin).

All RNA samples also contained an uncapped unpolyadenylated RNA (competitor RNA) that was included as a competitive inhibitor of RNase activity. Total RNA in each sample was adjusted to a total of 80 micrograms with competitor RNA. As a negative control (described below) DNAs expressing the luciferase protein under the control of a prokaryotic promoter were also injected. At 3 and 6 hours mice were given an intraperitoneal injection of luciferin (the substrate for the luciferase enzyme) and the light emitted from the mouse was measured.

Results summarized in Table 1

TABLE 1

| Nucleic Acid Used | Number of Mice (N) | Formulation | Relative Light Units (RLU/5 min) |
|---|---|---|---|
| Poly A RNA | 1 | 4 units of RNasin | $1.0 \times 10^6$ |
| Poly A RNA | 1 | 400 units of RNasin | $2.0 \times 10^7$ |
| Poly A signal RNA | 1 | 4 units of RNasin | $7.2 \times 10^4$ |
| Template DNA | 1 | none | signal at background |

The above results show that:

Injected RNA is transfected into the liver of living mice.

Capped polyadenylated RNA with a poly A tail (Poly A RNA) is translated in mouse livers because capped polyadenylated RNA gives a strong luciferase signal Capped RNA with a poly A signal (Poly A signal RNA) is translated in mouse livers but it gives a signal but it is about 100 fold lower than that seen with the RNA that has a poly A tail The RNAs used in all the experiments described here were transcribed from a bacterial promoter on a DNA plasmid. This promoter should not function efficiently in mammalian cells. The DNA template was removed after transcription using a DNase, however there is always the concern that the signal seen could be the result of DNA contamination. To control for this, an amount of template DNA equivalent to that used in the transcription was injected. If the signal is due to DNA contamination then this sample should give a signal. However, no signal is seen from the DNA control.

It was also found that addition of an RNase inhibitor (called RNasin) protects the RNA from degradation by serum nucleases, thus increasing the observed signal, because addition of RNasin increased the signal by 20 fold at the dose used.

From the above, the following conclusions are drawn. Hydrodynamic delivery of naked RNA results in high level transfer of RNA into the livers of living mice. Furthermore, capped and polyadenylated RNA works better than RNA with a polyadenylation signal but no poly A tail, although both RNAs gave a signal. Addition of an RNase inhibitor protected the RNA from degradation, resulting in a higher luciferase signal. Finally, the signal seen with the injected RNA is not due to DNA contamination.

C. Refinement of System

RNAs coding for luciferase protein were injected into living mice with 1) high or low doses of native or recombinant RNasin or 2) after treatment with RNase T1 which should destroy the RNA and abolish the signal (negative control). All RNA samples also contained an uncapped unpolyadenylated competitor RNA such that the total amount of RNA injected was 80 micrograms. Control DNAs expressing the luciferase protein under the control of a prokaryotic promoter were also injected in indicated control reactions. At 3 and 6 hours mice were given an intraperitoneal injection of luciferin and the light emitted from the mouse was measured. This experiment is largely to verify the results of the first experiment and to test which parameters are important. At the six hour timepoint, one mouse that had been injected with RNA was sacrificed and its organs were removed to determine which organs express luciferase.

The results are summarized in Table 2

When an amount of template DNA equivalent to that used in the transcription is injected without DNase treatment, no signal is seen, demonstrating that the signal is not due to DNA contamination.

Liver is the only site of luciferase expression.

From the above, the following conclusions are drawn. RNasin dose effects the level of expression. Both recombinant and native RNasin protect the injected RNA. No signal was seen when template DNA was injected or when RNA was destroyed with RNase, demonstrating that signal is not the result of DNA contamination. Finally, liver is the only site of luciferase expression.

D. Competitor RNA Enhances the Activity.

Luciferase activity from 20 micrograms of capped and polyadenylated luciferase RNA was measured. Four condi-

TABLE 2

| Nucleic Acid Used | micro-grams of RNA or DNA | Number of Mice (N) | Formulation | Relative Light Units (RLU/5 min) 3 hours | Relative Light Units (RLU/5 min) 6 hours | Relative Light Units (RLU/5 min) 24 hours |
|---|---|---|---|---|---|---|
| Poly A RNA | 50 | 1 | 240 units RNasin (Native) | $1.8 \times 10^5$ $1.6 \times 10^6$ | $1.1 \times 10^8$ $5.4 \times 10^5$ | Background Background |
| Poly A RNA | 50 | 1 | 44 units RNasin (Native) | $5.5 \times 10^4$ | $1.9 \times 104$ | |
| Poly A RNA | 10 | 1 | 240 units RNasin (Recombinant) | $7.7 \times 10^4$ | $1.8 \times 105$ | |
| Poly A RNA | 50 | 2 | 3000 units RNase T1 | Background | Background | |
| Template DMA | 2 | 1 | none | Background | Background | |

The above results demonstrate that:

The dose of RNasin alters the level of expression seen because increasing doses of RNasin lead to increased levels of luciferase activity.

Both native and recombinant RNasin both protect the RNA.

When the RNA is destroyed with RNase, the signal is abolished, demonstrating that the RNA is responsible for the signal (negative control).

tions were tested in experiments similar to those described in experiments 1 and 2:

1) 400 units of RNasin+competitor RNA;
2) 40 units of RNasin with no competitor RNA;
3) 800 units of RNasin with no competitor RNA;
4) 1200 units of RNasin with no competitor RNA.

At 3, 6 and 9 hours mice were given an intraperitoneal injection of luciferin and the light emitted from the mouse was measured.

The results are summarized in Table 3.

TABLE 3

| | Micro-grams Competitor RNA | Units of RNasin | Number of Mice (N) | Average (RLU/2 min) 3 hours | Average (RLU/2 min) 6 hours | Average (RLU/2 min) 9 hours |
|---|---|---|---|---|---|---|
| RLU standard error | 60 | 400 | 3 | $7.6 \times 10^4$ $3.5 \times 10^4$ | $1.7 \times 10^4$ $4.2 \times 10^3$ | $3.5 \times 10^3$ $9.6 \times 10^2$ |
| RLU standard error | None | 400 | 3 | $6.5 \times 10^3$ $1.4 \times 10^3$ | $4.2 \times 10^3$ $2.8 \times 10^3$ | $2.6 \times 10^3$ $1.7 \times 10^3$ |
| RLU standard error | None | 800 | 3 | $6.2 \times 10^4$ $3.1 \times 10^4$ | $8.7 \times 10^3$ $2.5 \times 10^3$ | $2.0 \times 10^3$ $3.7 \times 10^2$ |
| RLU standard error | None | 1200 | 3 | $7.6 \times 10^4$ $5.4 \times 10^4$ | $2.2 \times 10^4$ $1.6 \times 10^4$ | $7.4 \times 10^3$ $4.5 \times 10^3$ |

The above results demonstrate that:

RNasin dose alters the luciferase activity because increasing doses of RNasin lead to increasing luciferase activity. The highest dose (1200 units of RNasin) gave the highest activity at all times tested.

The addition of competitor RNA enhanced the measured luciferase activity, because presence of the competitor RNA enhanced the luciferase activity. This effect was synergistic with the protective effect of the RNasin.

From the above results, the following conclusions are drawn. Addition of competitor RNA increases luciferase signal. Furthermore, increasing doses of RNasin lead to increasing levels of luciferase activity E. Cap Independent Translation of Luciferase Using an Internal Ribosome Entry Site.

In Eukaryotes, translation of RNAs into protein occurs by two different mechanisms called cap dependent and cap independent translation. Cap independent translation requires a 5' nontranslated region called an internal ribosome entry site (IRES). Several RNA viruses, such as hepatitis C virus (HCV), polio virus and hepatitis A utilize IRES sequences to carry out cap independent translation. We originally developed the RNA transfection method described here with the idea that it could be used to make a small animal model system for studying anti-HCV therapeutics. Transfection with IRES RNAs could also be used for mutagenesis studies designed to investigate sequence elements necessary for efficient IRES function.

1 Description of Experiment and Results:

The RNA HCVluc has the HCV IRES at the 5' end and the luciferase gene followed by a poly A tail. 40 micrograms of HCVluc+40 micrograms of competitor RNA+20 microliters of RNasin were injected into the tail vain of the mice. At 3 and 6 hours mice were given an intraperitoneal injection of luciferin and the light emitted from the mouse was measured. Result: The HCV IRES was able to drive translation of the injected HCV luciferase RNA fusion. Quantitation of the results is summarized in Table 4.

TABLE 4

|  | 3 hours post injection | 6 hours post injection |
| --- | --- | --- |
| Average Relative Light Units | 1 7 x 10 | $4.6 \times 10^4$ |
| Standard Error | $7.4 \times 10^4$ | $1.6 \times 10^4$ |

F. Measurable Serum Concentrations of Human Factor IX (hFIX) Protein can be Produced and secreted upon injection of hFIX RNA.

Human factor IX protein is a blood clotting protein that is not produced by some patients with hemophilia. The levels of this protein in serum can be easily measured using an enzyme linked immunoassay (ELISA). We chose to express this protein for two reasons:

1) hFIX is a therapeutically relevant protein. Although transient expression of hFIX is not clinically relevant, it would be desirable to transiently express some other types of therapeutic proteins that do not require chronic expression.
2) hFIX is a human protein and is thus capable of eliciting an immune response in mice.

One application of RNA injection is in the development and testing of vaccines. An immune response to hFIX upon injection of hFIX RNA would demonstrate the proof of principle of using RNA as a vaccine.

1. Description of Experiment and Results:

40 micrograms of capped and polyadenylated hFIX RNA+40 micrograms of competitor RNA+800 units of RNasin were injected by tail vain into 1 mouse. Result: 40 nanograms/milliliter of serum were detected by ELISA at 6 hours. This amount of hFIX is within the significant range of the ELISA assay.

G. Hydrodynamic Delivery of HCV Genomic RNAs to Create an HCV Mouse Model

Two groups of 6 mice were injected with:

1) 50 micrograms of capped HCV full length genomic RNA called 90 FL HCV (which also contains some uncapped RNA)+40 micrograms of capped and polyadenylated hFIX RNA+400 units of RNasin; or
2) a full length non-infectious HCV genomic RNA that has a mutation in the replicase gene that makes it catalytically inactive (called 101 FL HCV)+40 micrograms of capped and polyadenylated hFIX RNA+400 units of RNasin.

The transcription templates for making the HCV RNAs were obtained from Charles Rice and Washington University. Six hours after injection the mice were bled and hFIX levels are being measured to normalize for injection efficiency. The injected HCV RNAs are expected to degrade rapidly. Any RNA detected after a few days is likely to be RNA newly synthesized during viral replication. A quantitative real time PCR method has been developed to measure the levels of HCV RNA in the livers of these mice. If replication of the virus occurs, then the levels of HCV RNAs in the mice injected with 90 FL HCV will be greater than the levels in mice injected with 101 FL HCV when measured weeks after injection. A histological, assay is also being developed in order to assay for the synthesis of HCV proteins. Three different positive outcomes are possible 1) The RNA enters the liver but is not translated and does not replicate 2) the RNA enters the liver and is translated but, does not replicate 3) the RNA enters the liver, is translated and replicates. All three outcomes are useful model systems. If 1, 2 or 3 occurs then this system could be used to test ribozymes directed against HCV RNAs (see experiment 9 below). If 2 or 3 occurs then, the this system could be used to test inhibitors of HCV translation, replication and infection.

Injection of this RNA did not result in a viral replication cycle for HCV. However, another group has used a similar method to initiate a hepatitis delta replication cycle. See Chang J, Sigal LJ, Lerro A, Taylor J., J Viro 1.75(7):3469-73 (2001).

H. In Vivo Cleavage of HCV RNAs by Ribozymes

DNAzymes targeting the IRES of HCV have been chemically synthesized. We hydrodynamically injected these ribozymes into mice and assessed their ability to decrease the levels of injected HCV RNAs within the liver. Five nanomoles of DNAzyme targetting the IRES was coinjected with 20 μg of an RNA comprised of the HCV IRES followed by the firefly luciferase coding sequence followed by 30 adenosines. The sequence of the DNAzyme was 5'-GAGGTTTAGGAG-GCTAGCTACAACGATCGTGCTCA-3' (SEQ ID NO:013). Mice that received the DNAzyme in combination with the target RNA emitted 95% less light at 6 hours than mice that received the target RNA alone. Conclusion: We demonstrated that this DNAzyme can inhibit translation from the HCV IRES, presumably by cleaving the IRES RNA sequence. Synthetic ribozymes were also tested using an analogous methodology and were found to be ineffective.

I. This experiment is to do a timecourse of luciferase expression after a single injection of capped and polyadenylated RNA. If the following condition is met, then we can use a first order exponential decay fit (described by Equation 1) of the data to calculate the degradation rate of the expressed protein. In order for this data to be fit to a simple first order exponential decay, the half life of the mRNA must be significantly less than the halflife of the protein (at least 5-10 fold less). If this condition is not met, then a more complex mathematical relationship that takes into account the halflife of the mRNA can be used. Another solution to this problem is to decrease the half life of the mRNA by making it uncapped or omiting the competitor RNA.

If we define the amount of protein at a given time (or the signal from the protein) as A, the amount of protein (or signal) at the first timepoint as Ao, the decay rate constant as k and time after the first measurement as t, the equation would be of the form $$A = Ao \exp^{(-kt)} \quad \text{(Equation 1)}$$

1. Description of the Experiment:

Four groups of 6 mice were injected with 20 micrograms of capped polyadenylated luciferase RNA+60 micrograms of uncapped competitor RNA+800 units of RNasin. At 3, 6, 9 or 24 hours, the mice were given an intraperitoneal injection of luciferin (1.5 micrograms/gram body weight) and the light emitted from the mouse was measured.

The results are provided in the table below:

|   | Hours Post | Light Units | Standard | Standard Error |
|---|---|---|---|---|
| 1 | 3.000 | 530000.000 | 330000.000 | 150000.000 |
| 2 | 6.000 | 200000.000 | 88000.000 | 36000.000 |
| 3 | 9.000 | 110000.000 | 43000.000 | 18000.000 |
| 4 | 24.000 | 1900.000 | 1100.000 | 440.000 |

Relative light units were plotted vs. time and the resulting curve is fit to Equation 1. This analysis yields an apparent degradation rate consant of 0.297 hour −1.

The most common method for measuring a half-life of a protein is the following. In one approach, the protein is purified and sometimes labeled (for example with radioactive iodine). The purified protein is injected and at different times the animal is sampled and the amount of protein remaining at any given time is plotted vs. time and the curve is fit to an equation such as Equation 1. The advantage of our method is that it does not require the in vitro synthesis or purification of the protein.

J. We have constructed RNAs that contain regulatory regions of the HCV RNA controlling the translation of a protein called luciferase (referred to here as HCV luc RNA). We have also constructed DNA expression plasmids that express similar RNAs once they enter cells (referred to here as HCV luc DNA). See FIG. 3 for diagrams of these constructs.

When either the HCV luc RNAs or the HCV luc DNAs are transfected into mice, they go to the liver and HCV luc RNAs or RNAs transcribed from the HCV luc DNAs are translated into luciferase protein. At various times, the substrate of the luciferase protein, luciferin, is injected into the mice. The enzyme luciferase consumes the luciferin and makes light in the process. The amount of light emitted from the mice is proportional to the amount of luciferase protein present at the time of the sampling.

We have synthesized short synthetic oligonucleotides of a type known as Morpholino oligos. We mixed 1 nanomol of a morpholino oligo with 10 micrograms of HCV luc RNA or 1 microgram of HCV luc DNA. The morpholino oligo was made by Gene Tools, LLC in Corvallis, Oregon and has the sequence 5'-TCTTTGAGGTTTAGGATTCGTGCTC-3' (SEQ ID NO:14). This mixture is then added to 1.8 milliliters of buffer and injected under high pressure into the tail veins of mice as described in our previous application. As a control, mixtures that do not contain the inhibitor are injected into other mice. In the presence of inhibitor, emitted light is reduced by more than 90%. We conclude from this finding that translation of the injected RNA or translation of the RNA produced from the injected DNA is prevented by the inhibitor by an antisense mechanism. In the case of the injected RNA we can only follow this inhibition for about 24 hours, because of the limited stability of the RNA in cells. In the case of the injected DNA, we can monitor translation for about 8 days. The translational inhibition lasted for the whole duration of the time we could measure translation in this system.

K.
Experiment A
control group: RNAs containing the HCV IRES and a
   luciferase reporter sequence are injected into mice and they
   glow when this RNA is translated into luciferase protein
Test Group:
Coinject inhibitor with RNA. Both go to the same cells.
   Inhibition is expressed as activity (glowing) compared to
   control group.
Experiment B
   Same as experiment A except we inject a DNA that encodes the target RNA along with the inhibitor. The DNA goes to the nucleus of the mouse hepatocytes and is transcribed to give the target RNA. This RNA goes to the cytoplasm of the cells where it interacts with the inhibitor.

The constructs employed in these experiments are provided in FIG. 4. The results of these experiments with antisense and DNAzyme inhibitors are provided in FIGS. 5A to 5F.

III. Inhibition of Hepatitis B Virus Replication in Mice by RNA Interference

A. Methods

1. Plasmids pTHBV2 (as described in Marion et al., *In Frontiers in Viral Hepatitis*. (ed. R. F. Schinazi, C. R., and J-P. Sommadossi) 197-209 (Elsevier Science, Amsterdam, 2002)) contains the HBV genome plus a redundancy for the sequences between nucleotides 1067 and 1996 of the HBV genome. HBVU6 RNAi plasmids were cloned using methods described at the website produced by placing http:// before and "cshl.org:9331/RNAi/docs/Web version of PCR strategy1.pdf" after "katahdin.".

Target sequences are as follows:

```
                                            (SEQ ID NO: 15)
HBVU6#1 = 5'-TCGTGGTGGACTTCTCTCAATTTTC-3', (SEQ ID NO: 16)
HBVU6#2 = 5'-CTCAGTTTACTAGTGCCATTTGTTC-3', (SEQ ID NO: 17)
HBVU6#3 = 5'-ATGATGTGGTATTGGGGGCCAAGTC-3', (SEQ ID NO: 18)
HBVU6#4 = 5'-TGGCCAAAATTCGCAGTCCCCAACC-3', (SEQ ID NO: 19)
HBVU6#5 = 5'-TCCCCGTCTGTGCCTTCTCATCTGC-3', (SEQ ID NO: 20)
HBVU6#6 = 5'-CCTAGAAGAAGAACTCCCTCGCCTC-3', (SEQ ID NO: 21)
HBVU6#7 = 5'-AGAAGATCTCAATCTCGGGAATCTC-3'.
```

2. Southern Blot Analysis

Total liver DNA was extracted and 10 μg of total DNA was digested with 40 units each of Dpn I (Roche, Indianapolis, Ind.) and Sac I (NEB, Beverly, Mass.) for 4 hours. Samples were boiled for 5 min in 50% formamide, then placed on ice such that all replicative forms migrate as a single band. This action was necessary in order to increase the sensitivity of the Southern blot sufficiently to detect HBV genomes. Samples were separated by 1.5% agarose gel electrophoresis, and assessed by Southern blot analysis. A standard curve was generated by "spiking in" indicated amounts of Eco RI digested pGEMayw. 2× plasmid DNA containing two head-to-tail tandem copies of HBVayw genomic DNA (ayw genotype) into 10 µg naive liver DNA. Standards were digested as described above. To demonstrate that the Dpn I digestion conditions were sufficient to degrade all plasmid DNA present in experimental samples, 1 copy per cell of pGEMayw.2× was added to 10 µg of naïve total DNA and digested as described. Separated DNA was transferred to a nylon membrane and probed with $^{32}$P labeled, whole HBV genomic DNA.

3. HBcAg Immunohistochemistry and Haat Measurements

Staining was carried out (as described in Ohashi et al., Nat. Med. (2000) 6:327-331) with 1:5000 and 1:250 dilutions of primary and secondary antibody, respectively. hAAT levels were measured by enzyme linked immunoassay as described in Yant et al., Nat. Genet. (2000)25:35-41.

4. Cell Culture and Mouse Transfections

Calcium phosphate transfections were carried out using standard methods. Hydrodynamic transfections of plasmids in PBS were carried out as described in Zhang et al., Hum. Gene. Therap. (1999)10:1735-37; and Liu et al., Gene. Ther. (1999)6:1258-66. One mouse in the HBVU6#2 group expressed very low levels of hAAT, was considered poorly transfected and was excluded prior to analysis for HBV levels. 18-22 gram female BALB/c mice were obtained from Jackson Laboratory (Bar Harbor, Me.). Animals were treated according to NIH Guidelines for Animal Care and the Guidelines of Stanford University.

B. Results

Seven RNAi target sequences were chosen based on their conservation among the major HBV genotypes (adw, adw2 adr(1), adr(2) ayr, ayw(1) and ayw(2)) (McLachlan, A. *Molecular biology of the hepatitis B virus* (CRC Press, Boca Raton, Fla., 1991).) and inclusion of these sequences in overlapping reading frames of the virus such that multiple viral RNAs would be targeted by each shRNA. HBVU6#1, HBVU6#2, HBVU6#3 and HBVU6#4 target the HBV S-antigen and the HBV polymerase mRNAs. HBVU6#5 targets the X-region and the HBV polymerase mRNAs. HBVU6#6 and HBVU6#7 target the core antigen and polymerase mRNAs. Each shRNA also targets the antigenomic RNA that serves as the template for HBV genomic replication. shRNAs were cloned downstream of the human U6 promoter as previously described in Paddison et al., Genes Devel. (2002) 16:948-958.

In order to test whether RNAi could inhibit HBV in culture, a co-transfection assay was performed. In each experiment three plasmids were co-transfected into cultured HuH-7 cells, (a hepatocyte derived cell line); i) 4 µg of the plasmid pTHBV2 containing the HBV genome ii) 5 µg of a U6 shRNA expression vector (or either empty vector that does not express shRNAs or an shRNA vector targeting HCV (HCVU6) as negative controls), and iii) 5 µg of a plasmid (pThAAT) that expresses the secreted protein human α-1 antitrypsin (hAAT). Transfection with pTHBV2 initiates an HBV viral replication cycle, resulting in production of replicated HBV genomes as well as all viral mRNAs and proteins (including HBsAg and HBcAg). Enzyme linked immunoassay measurements of secreted hAAT served to monitor for transfection efficiency and non-specific translational inhibition or toxicity. Average serum hAAT levels at 72 hours were similar in all groups.

At days 3, 6 and 8, HBsAg levels in the media were measured (See FIG. 1). With the exception of HBVU6#1 (data not shown), treatment with each of the shRNA expression plasmids reduced the amount of HBsAg compared to the untreated control group (in three independent experiments). Treatment with HBVU6#2 and HBVU6#6 gave the greatest reduction in HBsAg (94.2%+/−0.59 and 91.5%+/−1.4, respectively at day 8) compared to the empty vector control. These results demonstrate that RNAi can significantly inhibit HBV in cultured cells.

Figure 2:
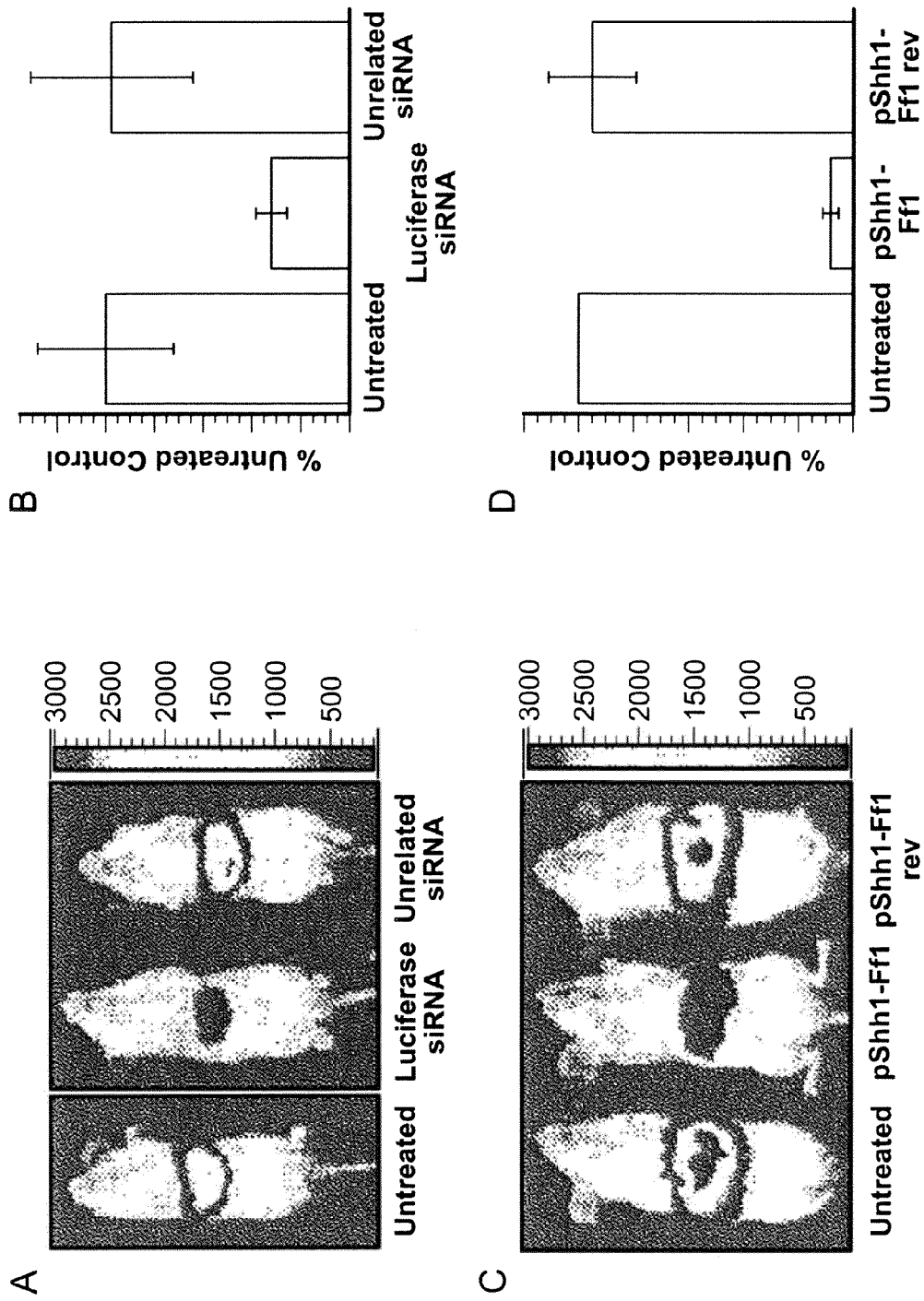
FIGS. 2A to 2D: RNA interference in adult mice.
Figure 5A:
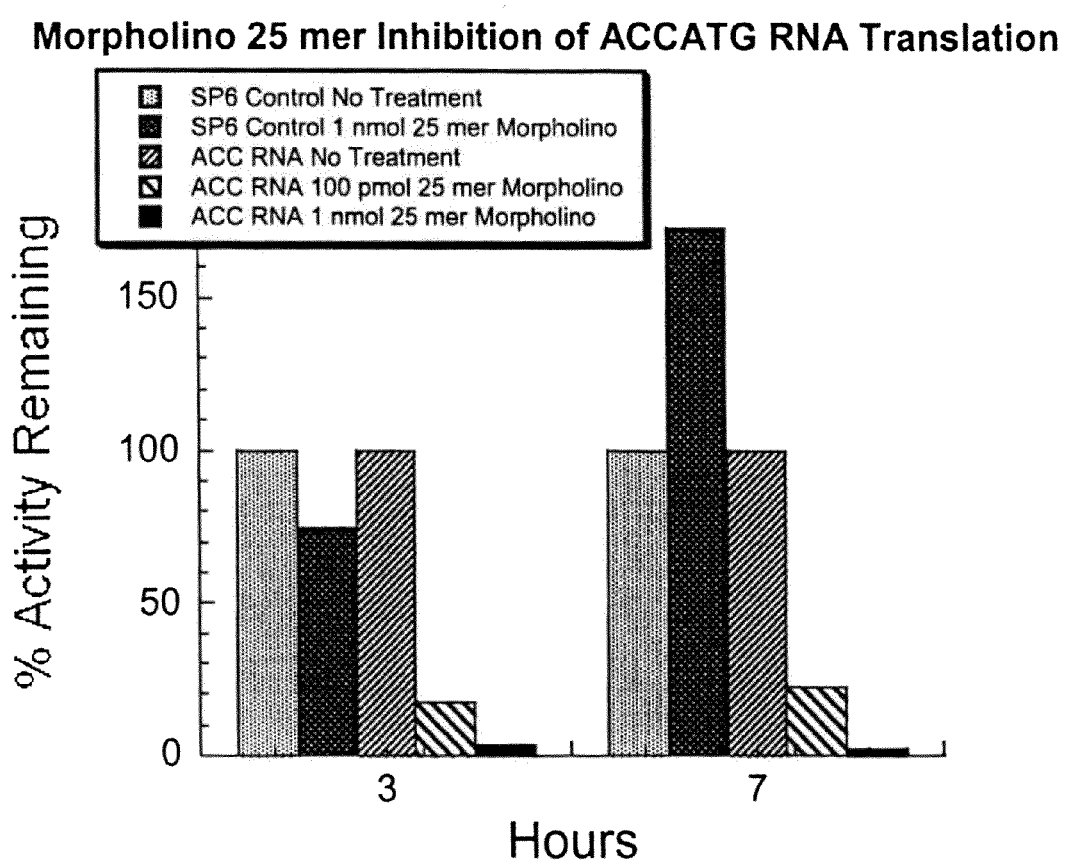
FIGS. 5A to 5F provide graphical results of a morpholino phosphoramidate antisense HCV inhibition assay performed according to the subject invention.
Figure 5B:
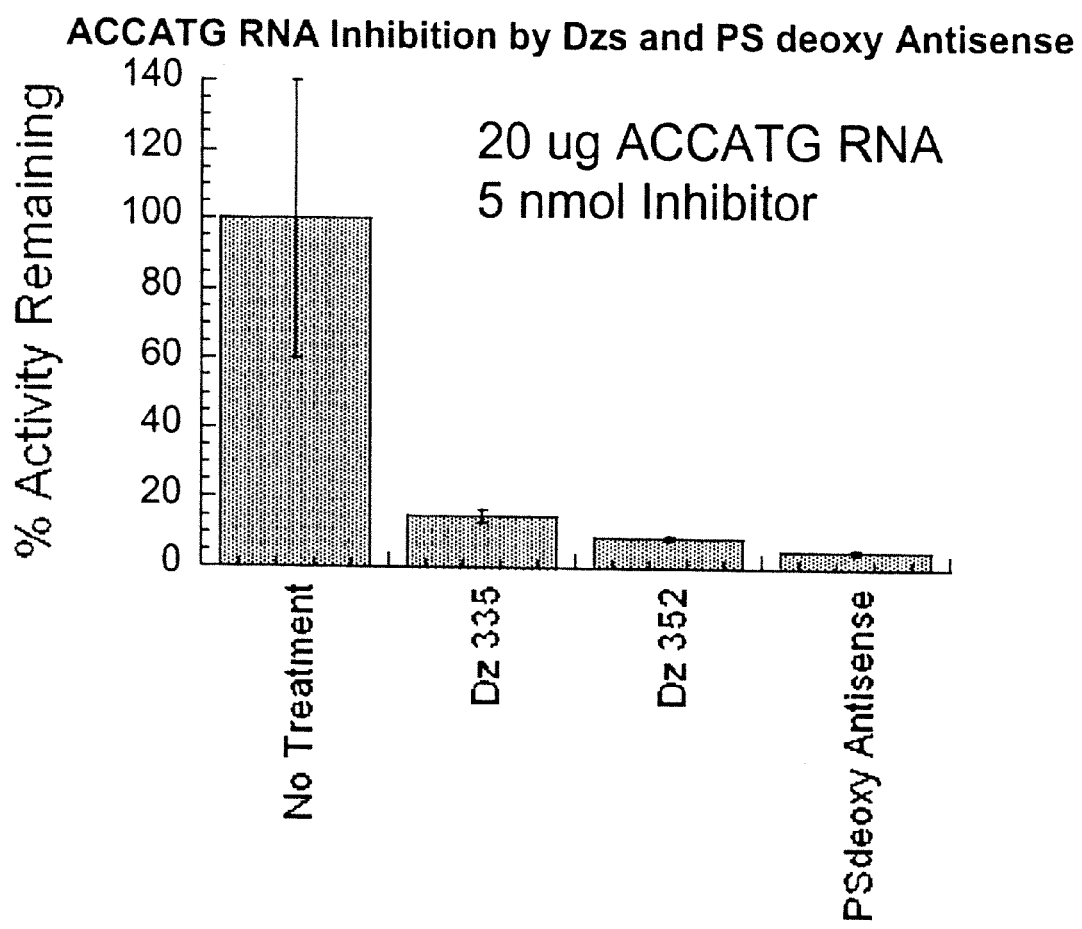
Figure 5C:
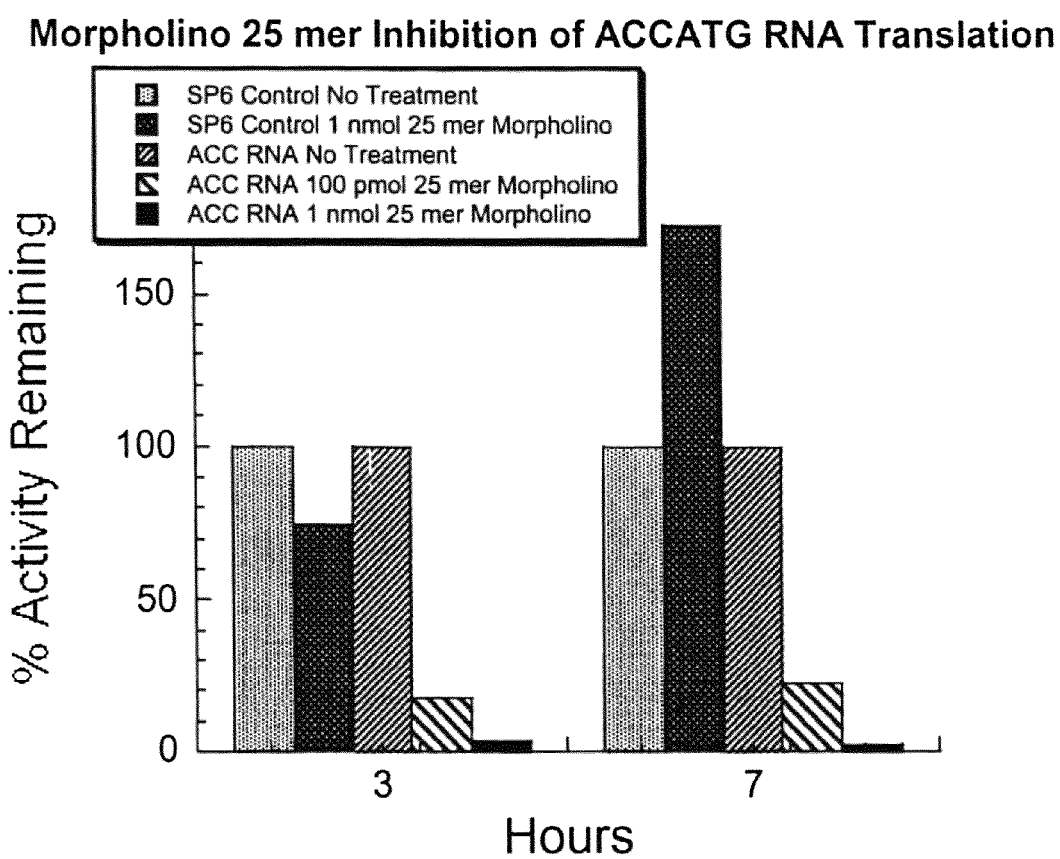
Figure 5D:
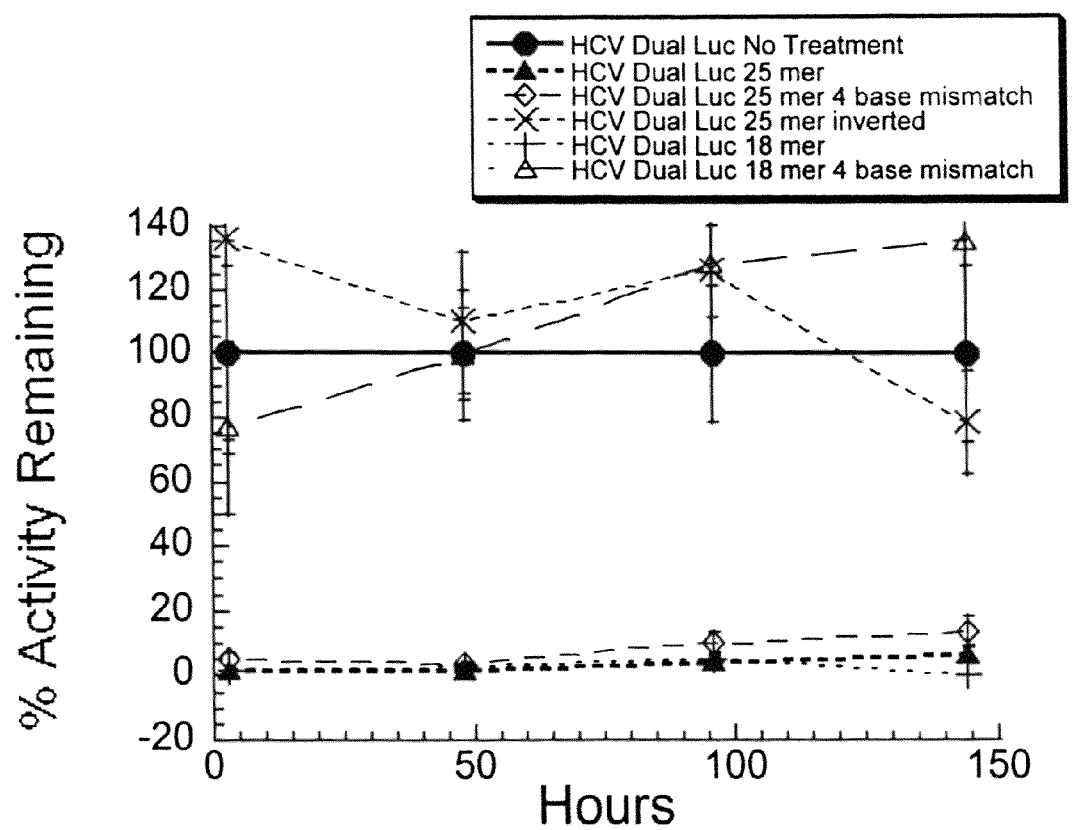
Figure 5E:
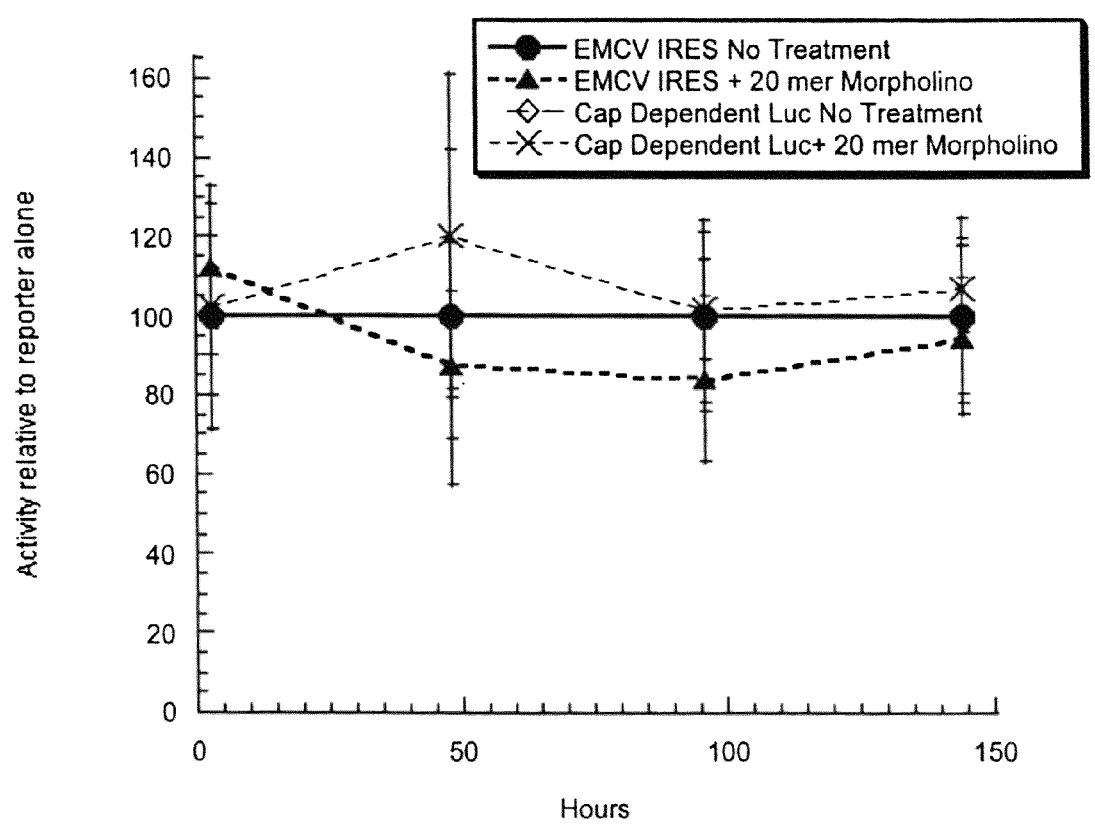
Figure 5F:
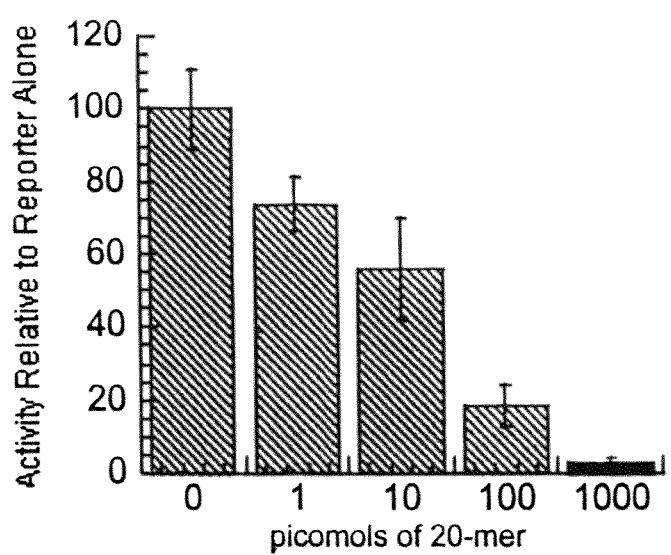
Figure 6:
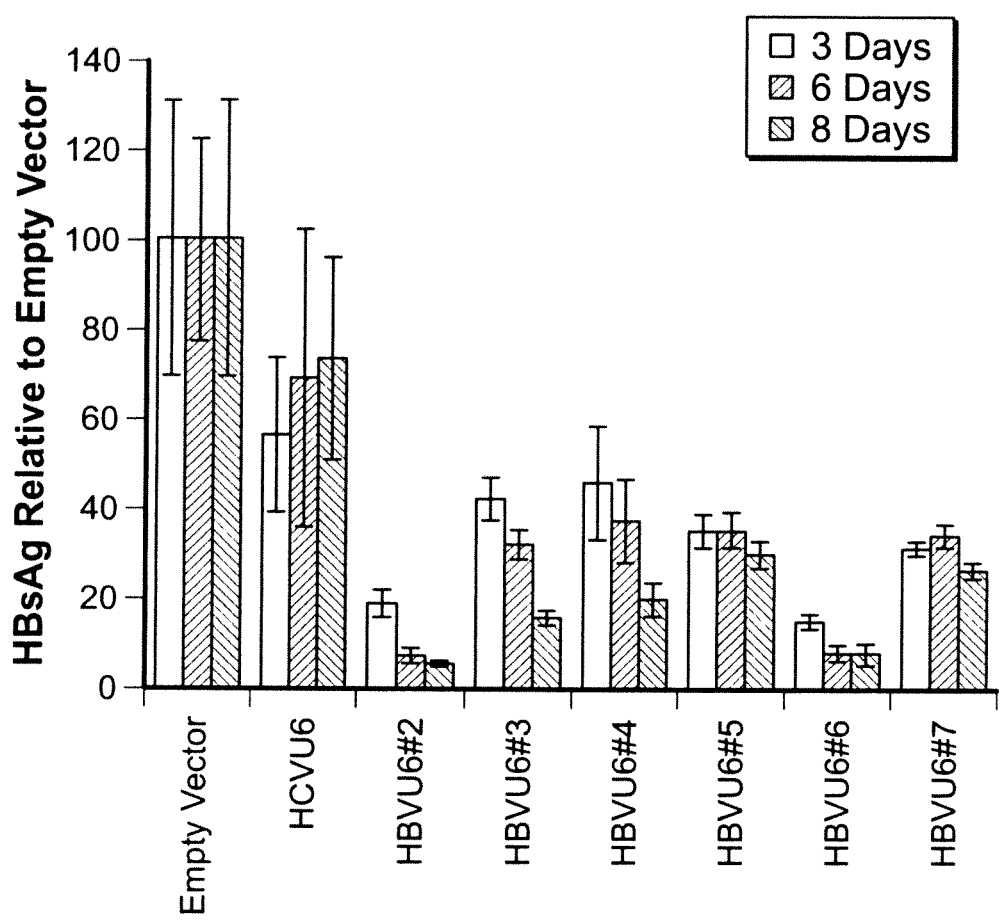
FIG. 6. HBsAg levels in culture media after treatment with shRNA expression plasmids. Standard errors are shown.
Figure 7:
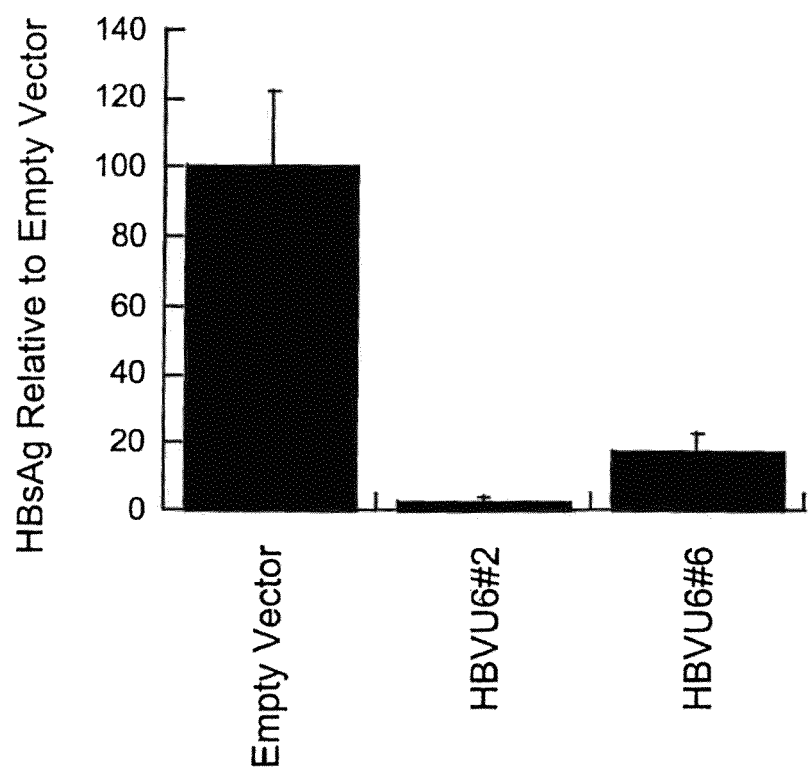
FIG. 7. HBsAg levels in mouse serum after treatment with the shRNA expression plasmids HBVU6#2 and HBVU6#6. Standard errors are shown.

The same three plasmid co-transfection model was used to test the ability of HBVU6#2 and HBVU6#6 to inhibit HBV in mice. In three independent experiments, mice were transfected with 5 µg HBVU6#2, HBVU6#6 or empty vector as well as 4 µg pTHBV2, and 3 µg pThAAT using hydrodynamic transfection, a method that results in gene transfer into 5 to 40% of mouse hepatocytes (N=5-6 mice per group). At day 2 or 3, serum hAAT were levels were measured to ensure that transfection efficiencies were similar. Average hAAT levels varied by less than two fold. At day 7, blood samples were obtained for serum HBsAg measurements, mice were sacrificed and liver tissue was preserved for Southern blot and histological analysis. FIG. 2 shows that serum HBsAg levels were reduced by 97.4%+/−1.3 and 83.3%+/−5.4 in mice that received HBVU6#2 and HBVU6#6, respectively (FIG. 2)), demonstrating that RNAi can inhibit the production of HBsAg in mice. Furthermore, since HBVU6#6 does not target the HBsAg mRNA, the reductions observed in HBsAg was likely due to inhibition of HBV viral replication.

HBcAg is a protein synthesized in infected cells and required for HBV viral replication. Consistent with the expected transfection efficiency, 5.2%+/−1.1 of cells stained for HBcAg in tissue sections from mice that received the empty vector and pTHBV2. Liver sections from mice receiving HBVU6#2 had dramatically reduced numbers of HBcAg stained cells (reduced by 99.7%+/−0.3). Most fields had no stained cells, although there were rare hepatocytes with lightly stained nuclei. The number of stained hepatocytes in sections from HBVU7#2 treated mice was reduced by 94%+/−1.9. No staining was seen in sections from mice that did not receive pTHBV2. Importantly, the levels of tissue HBcAg and serum HBsAg in the different experimental groups correlated between assays. These results demonstrate that HBV RNAi can inhibit the production of HBV proteins. The fact that HBVU6#2 reduced HBcAg expression even though this RNAi does not directly target the HBcAg mRNA again suggests that the reduction in staining was due to inhibition of HBV viral replication.

To definitively determine if treatment with HBVU6#2 and HBVU6#6 resulted in a reduction in replicated viral genomes in transfected hepatocytes, a modified Southern Blot assay was performed that detects replicated viral genomes (Dpn I insensitive), but not bacterially methylated input plasmid (Dpn I sensitive). Size standards, intensity standards and controls are described in the figure legend. HBV genomic DNA was present in samples from mice in the control group that received the empty vector (lanes 6-11) while mice that received HBVU6#2 (lanes 12, 13) had undetectable levels of replicated HBV genomes (detection limit was <0.04 copies per cell). Total DNA samples from mice that received HBVU6#6 (lanes 14, 15) had significantly reduced replicative HBV genomic DNA molecules. HBV genome levels correlate well with serum HBsAg and tissue HBcAg measurements for these groups. These results show that RNAi directed against HBV results in significant reduction in the replication of HBV genomes.

C. Discussion

Three separate lines of evidence described above establish that RNAi significantly reduced HBV replication in mammals; i) upon RNAi expression, levels of secreted HBsAg in culture media and mouse serum were significantly diminished, ii) the amount of replicated HBV genomic DNA was reduced to undetectable levels, iii) as were the number of cells staining for HBcAg (intensity of staining was also decreased). Interestingly, the largest reduction in nuclei staining for HBcAg was seen with HBVU6#2 despite the fact that it does not target the HBcAg mRNA. Likewise, HBVU6#7 reduces the levels of HBsAg even though it does not target the HBsAg mRNA. This further supports the hypothesis that RNAi inhibited HBV viral replication.

RNAi can be directed to cleave any target RNA, providing a single methodology for rational drug design for many different diseases. For this reason RNAi has generated substantial interest. It is clear from our study that viral inhibition by RNAi in mammals is feasible. However, a recent manuscript by Gitlin et al. found poliovirus escape mutants after extended treatment with siRNAs, suggesting that multiple viral sequences must be targeted simultaneously in order to prevent the emergence of resistant strains.

The above screening protocol in which the inhibitor and RNA/DNA are coadministered offers important advantages in terms of allowing one to separate issues of drug delivery from issues of drug efficacy.

It is evident from the above results and discussion that the subject invention provides a viable way of using RNAi agents in non-embryonic mammalian organisms, where the subject methods and compositions can be employed for a variety, of different academic and therapeutic applications. In addition, the subject invention provides an improved method of transferring a nucleic acid into a target cell is provided by the subject invention. Specifically, the subject invention provides for a highly efficient in vivo method for naked nucleic acid transfer which does not employ viral vectors and therefore provides many advantages over prior art methods of nucleic acid transfer. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of reducing expression of a target RNA sequence in a non-embryonic mammal, said method comprising:
   administering to said mammal, in vivo, an effective amount of an RNAi agent, said RNAi agent being
   (i) a transcriptional template of an interfering ribonucleic acid, wherein the interfering ribonucleic acid is an shRNA of 66 to 78 nucleotides in length and comprises a duplex structure of 21 to 29 base pairs in length, and
   (ii) specific for a target RNA sequence present in a cell of the mammal.

2. The method according to claim 1, wherein said transcriptional template is a deoxyribonucleic acid.

3. The method according to claim 2, wherein said deoxyribonucleic acid encodes a non-translated RNA.

4. The method of claim 1, wherein the interfering ribonucleic acid comprising a duplex 21 base pairs in length.

5. The method of claim 1, wherein the interfering ribonucleic acid comprises a duplex structure 29 base pairs in length.

6. The method according to claim 1, wherein said non-embryonic mammal is an adult.

7. The method according to claim 1, wherein said non-embryonic mammal is a juvenile.

8. The method according to claim 1, wherein said RNAi agent is intravenously administered to said non-embryonic mammal.

9. The method according to claim 1, wherein the RNAi agent is administered to a peripheral vein of the mammal.

10. The method according to claim 9, wherein said RNAi agent is administered to said non-embryonic mammal in conjunction with an RNAse inhibitor.

11. The method of claim 1, wherein the target RNA sequence present in the cell is a genomic viral RNA sequence.

12. The method of claim 1, wherein the target RNA sequence present in the cell is a transcript encoded by an RNA or DNA virus.

13. The method of claim 1, wherein the target RNA sequence present in the cell is from an RNA viral infection.

14. The method of claim 1, wherein the target RNA sequence present in the cell is from an DNA viral infection.

15. The method of claim 13 or claim 14, wherein the viral infection is a hepatitis viral infection.

* * * * *